(12) United States Patent
Barron et al.

(10) Patent No.: US 12,018,801 B2
(45) Date of Patent: Jun. 25, 2024

(54) SINGLE DIODE DISINFECTION

(71) Applicant: Vyv, Inc., Latham, NY (US)

(72) Inventors: Robert Barron, Boulder, CO (US); Jorel Lalicki, Troy, NY (US); James W. Peterson, Port Washington, NY (US); Nicholas Jones, Mechanicville, NY (US); Cori J. Winslow, Rensselaer, NY (US)

(73) Assignee: Vyv, Inc., Latham, NY (US)

( * ) Notice: Subject to any disclaimer, the term of this patent is extended or adjusted under 35 U.S.C. 154(b) by 0 days.

(21) Appl. No.: 18/207,562

(22) Filed: Jun. 8, 2023

(65) Prior Publication Data
US 2023/0324014 A1     Oct. 12, 2023

Related U.S. Application Data

(63) Continuation of application No. 17/172,949, filed on Feb. 10, 2021, now Pat. No. 11,713,851, which is a
(Continued)

(51) Int. Cl.
*A61L 2/08*     (2006.01)
*F21K 9/64*     (2016.01)
(Continued)

(52) U.S. Cl.
CPC .............. *F21K 9/64* (2016.08); *A61L 2/082* (2013.01); *A61L 2/084* (2013.01); *H01L 33/502* (2013.01);
(Continued)

(58) Field of Classification Search
CPC ............................... H01L 33/504; A61L 2/084
(Continued)

(56) References Cited

U.S. PATENT DOCUMENTS

| 1,493,820 A | 5/1924 | Miller et al. |
| 2,622,409 A | 12/1952 | Stimkorb |

(Continued)

FOREIGN PATENT DOCUMENTS

| CN | 1932370 A | 3/2007 |
| CN | 201396611 Y | 2/2010 |

(Continued)

OTHER PUBLICATIONS

Nov. 6, 2020—(TW) Office Action w/Tr.—TW 108146777.
(Continued)

*Primary Examiner* — Christopher M Raabe
(74) *Attorney, Agent, or Firm* — Banner & Witcoff, Ltd.

(57) ABSTRACT

Methods, systems, and devices for inactivating microorganisms are disclosed. An example light emitting device that inactivates microorganisms on a surface comprises a light emitter configured to emit a first light comprising a first wavelength in a range of 380 nanometers (nm) to 420 nm, a first light-converting material configured to convert a first portion of the first light to at least a second light comprising a second wavelength different from the first wavelength, and a second light-converting material configured to convert a second portion of the first light to at least a third light comprising a third wavelength different from the first wavelength, wherein at least the first light, the second light, and the third light mix to form a disinfecting white light.

20 Claims, 9 Drawing Sheets

Related U.S. Application Data continuation of application No. 16/456,537, filed on Jun. 28, 2019, now Pat. No. 10,918,747, which is a continuation of application No. 15/886,366, filed on Feb. 1, 2018, now Pat. No. 10,357,582, which is a continuation-in-part of application No. 15/223,134, filed on Jul. 29, 2016, now Pat. No. 9,927,097.

(60) Provisional application No. 62/198,726, filed on Jul. 30, 2015.

(51) Int. Cl.
| | |
|---|---|
| H01L 33/50 | (2010.01) |
| H05B 45/20 | (2020.01) |
| F21V 9/30 | (2018.01) |
| F21Y 115/10 | (2016.01) |
| H01L 33/52 | (2010.01) |

(52) U.S. Cl.
CPC .......... *H05B 45/20* (2020.01); *A61L 2202/11* (2013.01); *F21V 9/30* (2018.02); *F21Y 2115/10* (2016.08); *H01L 33/52* (2013.01)

(58) Field of Classification Search
USPC .................................................... 422/22
See application file for complete search history.

(56) References Cited

U.S. PATENT DOCUMENTS

| | | | |
|---|---|---|---|
| 2,773,715 | A | 12/1956 | Lindner |
| 3,314,746 | A | 4/1967 | Millar |
| 3,670,193 | A | 6/1972 | Thorington et al. |
| 3,791,864 | A | 2/1974 | Steingroever |
| 3,926,556 | A | 12/1975 | Boucher |
| 3,992,646 | A | 11/1976 | Corth |
| 4,121,107 | A | 10/1978 | Bachmann |
| 4,461,977 | A | 7/1984 | Pierpoint et al. |
| 4,576,436 | A | 3/1986 | Daniel |
| 4,867,052 | A | 9/1989 | Cipelletti |
| 4,892,712 | A | 1/1990 | Robertson et al. |
| 4,910,942 | A | 3/1990 | Dunn et al. |
| 5,231,472 | A | 7/1993 | Marcus et al. |
| 5,489,827 | A | 2/1996 | Xia |
| 5,530,322 | A | 6/1996 | Ference et al. |
| 5,559,681 | A | 9/1996 | Duarte |
| 5,668,446 | A | 9/1997 | Baker |
| 5,721,471 | A | 2/1998 | Begemann et al. |
| 5,725,148 | A | 3/1998 | Hartman |
| 5,800,479 | A | 9/1998 | Thiberg |
| 5,901,564 | A | 5/1999 | Comeau, II |
| 5,915,279 | A | 6/1999 | Cantrall et al. |
| 5,962,989 | A | 10/1999 | Baker |
| 5,968,766 | A | 10/1999 | Powers |
| 6,031,958 | A | 2/2000 | McGaffigan |
| 6,166,496 | A | 12/2000 | Lys et al. |
| 6,183,500 | B1 | 2/2001 | Kohler |
| 6,242,752 | B1 | 6/2001 | Soma et al. |
| 6,246,169 | B1 | 6/2001 | Pruvot |
| 6,251,127 | B1 | 6/2001 | Biel |
| 6,379,022 | B1 | 4/2002 | Amerson et al. |
| 6,477,853 | B1 | 11/2002 | Khorram |
| 6,524,529 | B1 | 2/2003 | Horton, III |
| 6,551,346 | B2 | 4/2003 | Crossley |
| 6,554,439 | B1 | 4/2003 | Teicher et al. |
| 6,627,730 | B1 | 9/2003 | Burnie |
| 6,676,655 | B2 | 1/2004 | McDaniel |
| 6,791,259 | B1 | 9/2004 | Stokes et al. |
| 6,902,807 | B1 | 6/2005 | Argoitia et al. |
| 7,015,636 | B2 | 3/2006 | Bolta |
| 7,175,807 | B1 | 2/2007 | Jones |
| 7,190,126 | B1 | 3/2007 | Paton |
| 7,198,634 | B2 | 4/2007 | Harth et al. |
| 7,201,767 | B2 | 4/2007 | Bhullar |
| 7,213,941 | B2 | 5/2007 | Sloan et al. |
| 7,438,719 | B2 | 10/2008 | Chung et al. |
| 7,476,885 | B2 | 1/2009 | Garcia et al. |
| 7,503,675 | B2 | 3/2009 | Demarest et al. |
| 7,516,572 | B2 | 4/2009 | Yang et al. |
| 7,521,875 | B2 | 4/2009 | Maxik |
| 7,611,156 | B2 | 11/2009 | Dunser |
| 7,612,492 | B2 | 11/2009 | Lestician |
| 7,658,891 | B1 | 2/2010 | Barnes |
| 7,955,695 | B2 | 6/2011 | Argoitia |
| 8,035,320 | B2 | 10/2011 | Sibert |
| 8,214,084 | B2 | 7/2012 | Ivey et al. |
| 8,232,745 | B2 | 7/2012 | Chemel et al. |
| 8,357,914 | B1 | 1/2013 | Caldwell |
| 8,398,264 | B2 | 3/2013 | Anderson et al. |
| 8,467,052 | B1 | 6/2013 | Chao et al. |
| 8,476,844 | B2 | 7/2013 | Hancock et al. |
| 8,481,970 | B2 | 7/2013 | Cooper et al. |
| 8,506,612 | B2 | 8/2013 | Ashdown |
| 8,508,204 | B2 | 8/2013 | Deurenberg et al. |
| 8,761,565 | B1 | 6/2014 | Coleman et al. |
| 8,886,361 | B1 | 11/2014 | Harmon et al. |
| 8,895,940 | B2 | 11/2014 | Moskowitz et al. |
| 8,999,237 | B2 | 4/2015 | Tumanov |
| 9,024,276 | B2 | 5/2015 | Pugh et al. |
| 9,027,479 | B2 | 5/2015 | Raksha et al. |
| 9,028,084 | B2 | 5/2015 | Maeng et al. |
| 9,039,966 | B2 | 5/2015 | Anderson et al. |
| 9,046,227 | B2 | 6/2015 | David et al. |
| 9,078,306 | B2 | 7/2015 | Mans et al. |
| 9,119,240 | B2 | 8/2015 | Nagazoe |
| 9,173,276 | B2 | 10/2015 | Van Der Veen et al. |
| 9,257,059 | B2 | 2/2016 | Raksha et al. |
| 9,283,292 | B2 | 3/2016 | Kretschmann |
| 9,313,860 | B2 | 4/2016 | Wingren |
| 9,323,894 | B2 | 4/2016 | Kiani |
| 9,333,274 | B2 | 5/2016 | Peterson et al. |
| 9,368,695 | B2 | 6/2016 | David et al. |
| 9,410,664 | B2 | 8/2016 | Krames et al. |
| 9,420,671 | B1 | 8/2016 | Sugimoto et al. |
| 9,433,051 | B2 | 8/2016 | Snijder et al. |
| 9,439,271 | B2 | 9/2016 | Ku et al. |
| 9,439,989 | B2 | 9/2016 | Lalicki et al. |
| 9,492,576 | B1 | 11/2016 | Cudak et al. |
| 9,581,310 | B2 | 2/2017 | Wu et al. |
| 9,623,138 | B2 | 4/2017 | Pagan et al. |
| 9,625,137 | B2 | 4/2017 | Li et al. |
| 9,681,510 | B2 | 6/2017 | van de Ven |
| 10,806,812 | B2 | 10/2020 | Barron et al. |
| 11,395,858 | B2 | 7/2022 | Barron et al. |
| 2002/0074559 | A1 | 6/2002 | Dowling et al. |
| 2002/0122743 | A1 | 9/2002 | Huang |
| 2003/0009158 | A1 | 1/2003 | Perricone |
| 2003/0019222 | A1 | 1/2003 | Takahashi et al. |
| 2003/0023284 | A1 | 1/2003 | Gartstein et al. |
| 2003/0124023 | A1 | 7/2003 | Burgess et al. |
| 2003/0178632 | A1 | 9/2003 | Hohn et al. |
| 2003/0207644 | A1 | 11/2003 | Green et al. |
| 2003/0222578 | A1 | 12/2003 | Cok |
| 2003/0231485 | A1 | 12/2003 | Chien |
| 2004/0008523 | A1 | 1/2004 | Butler |
| 2004/0010299 | A1 | 1/2004 | Tolkoff et al. |
| 2004/0024431 | A1 | 2/2004 | Carlet |
| 2004/0039242 | A1 | 2/2004 | Tolkoff et al. |
| 2004/0047142 | A1 | 3/2004 | Goslee |
| 2004/0147984 | A1 | 7/2004 | Altshuler et al. |
| 2004/0147986 | A1 | 7/2004 | Baumgardner et al. |
| 2004/0158541 | A1 | 8/2004 | Notarianni et al. |
| 2004/0159039 | A1 | 8/2004 | Yates et al. |
| 2004/0162596 | A1 | 8/2004 | Altshuler et al. |
| 2004/0230259 | A1 | 11/2004 | Di Matteo |
| 2004/0262595 | A1 | 12/2004 | Mears et al. |
| 2004/0266546 | A1 | 12/2004 | Huang |
| 2005/0055070 | A1 | 3/2005 | Jones et al. |
| 2005/0104059 | A1 | 5/2005 | Friedman et al. |
| 2005/0107849 | A1 | 5/2005 | Altshuler et al. |
| 2005/0107853 | A1 | 5/2005 | Krespi et al. |
| 2005/0159795 | A1 | 7/2005 | Savage et al. |
| 2005/0207159 | A1 | 9/2005 | Maxik |
| 2005/0212397 | A1 | 9/2005 | Murazaki et al. |

(56) References Cited

U.S. PATENT DOCUMENTS

| | | |
|---|---|---|
| 2005/0253533 A1 | 11/2005 | Lys et al. |
| 2005/0267233 A1 | 12/2005 | Joshi |
| 2006/0006678 A1 | 1/2006 | Herron |
| 2006/0009822 A1 | 1/2006 | Savage et al. |
| 2006/0022582 A1 | 2/2006 | Radkov |
| 2006/0071589 A1 | 4/2006 | Radkov |
| 2006/0085052 A1 | 4/2006 | Feuerstein et al. |
| 2006/0138435 A1 | 6/2006 | Tarsa et al. |
| 2006/0186377 A1 | 8/2006 | Takahashi et al. |
| 2006/0230576 A1 | 10/2006 | Meine |
| 2006/0247741 A1 | 11/2006 | Hsu et al. |
| 2006/0262545 A1 | 11/2006 | Piepgras et al. |
| 2007/0023710 A1 | 2/2007 | Tom et al. |
| 2007/0061050 A1 | 3/2007 | Hoffknecht |
| 2007/0115665 A1 | 5/2007 | Mueller et al. |
| 2007/0164232 A1 | 7/2007 | Rolleri et al. |
| 2007/0208395 A1 | 9/2007 | Leclerc et al. |
| 2007/0258851 A1 | 11/2007 | Fogg et al. |
| 2008/0008620 A1 | 1/2008 | Alexiadis |
| 2008/0015560 A1 | 1/2008 | Gowda et al. |
| 2008/0091250 A1 | 4/2008 | Powell |
| 2008/0151533 A1 | 6/2008 | Genova |
| 2008/0278927 A1 | 11/2008 | Li et al. |
| 2008/0305004 A1 | 12/2008 | Anderson et al. |
| 2008/0307818 A1 | 12/2008 | Min et al. |
| 2009/0018621 A1 | 1/2009 | Vogler et al. |
| 2009/0034236 A1 | 2/2009 | Reuben |
| 2009/0076115 A1 | 3/2009 | Wharton et al. |
| 2009/0154167 A1 | 6/2009 | Lin |
| 2009/0231832 A1 | 9/2009 | Zukauskas et al. |
| 2009/0262515 A1 | 10/2009 | Lee et al. |
| 2009/0285727 A1 | 11/2009 | Levy |
| 2009/0314308 A1 | 12/2009 | Kim et al. |
| 2010/0001648 A1 | 1/2010 | De Clercq et al. |
| 2010/0027259 A1 | 2/2010 | Simon et al. |
| 2010/0071257 A1 | 3/2010 | Tsai |
| 2010/0090935 A1 | 4/2010 | Tseng et al. |
| 2010/0102252 A1 | 4/2010 | Harmon et al. |
| 2010/0107991 A1 | 5/2010 | Elrod et al. |
| 2010/0121420 A1 | 5/2010 | Fiset et al. |
| 2010/0148083 A1 | 6/2010 | Brown et al. |
| 2010/0179469 A1 | 7/2010 | Hammond et al. |
| 2010/0232135 A1 | 9/2010 | Munehiro et al. |
| 2010/0246169 A1 | 9/2010 | Anderson et al. |
| 2011/0063835 A1 | 3/2011 | Rivas et al. |
| 2011/0084614 A1 | 4/2011 | Eisele et al. |
| 2011/0256019 A1 | 10/2011 | Gruen et al. |
| 2011/0316025 A1 | 12/2011 | Kuzuhara et al. |
| 2012/0014538 A1 | 1/2012 | Bozkurt et al. |
| 2012/0025717 A1 | 2/2012 | Klusmann et al. |
| 2012/0043552 A1 | 2/2012 | David et al. |
| 2012/0161170 A1 | 6/2012 | Dubuc et al. |
| 2012/0199005 A1 | 8/2012 | Koji et al. |
| 2012/0273340 A1 | 11/2012 | Felix |
| 2012/0280147 A1 | 11/2012 | Douglas |
| 2012/0281408 A1 | 11/2012 | Owen et al. |
| 2012/0315626 A1 | 12/2012 | Nishikawa et al. |
| 2012/0320607 A1 | 12/2012 | Kinomoto et al. |
| 2013/0010460 A1 | 1/2013 | Peil et al. |
| 2013/0045132 A1 | 2/2013 | Tumanov |
| 2013/0077299 A1 | 3/2013 | Hussell et al. |
| 2013/0181246 A1 | 7/2013 | Wu |
| 2013/0200279 A1 | 8/2013 | Chuang |
| 2013/0298445 A1 | 11/2013 | Aoki et al. |
| 2013/0313516 A1 | 11/2013 | David et al. |
| 2013/0313546 A1 | 11/2013 | Yu |
| 2013/0323375 A1 | 12/2013 | Takahashi et al. |
| 2014/0043810 A1 | 2/2014 | Jo et al. |
| 2014/0061509 A1 | 3/2014 | Shur et al. |
| 2014/0209944 A1 | 7/2014 | Kim et al. |
| 2014/0225137 A1 | 8/2014 | Krames et al. |
| 2014/0254131 A1 | 9/2014 | Osinski et al. |
| 2014/0265868 A1 | 9/2014 | Morrisseau |
| 2014/0301062 A1 | 10/2014 | David et al. |
| 2014/0328046 A1 | 11/2014 | Aanegola et al. |
| 2014/0334137 A1 | 11/2014 | Hasenoehrl et al. |
| 2014/0362523 A1 | 12/2014 | Degner et al. |
| 2015/0049459 A1 | 2/2015 | Peeters et al. |
| 2015/0062892 A1 | 3/2015 | Krames et al. |
| 2015/0068292 A1 | 3/2015 | Su et al. |
| 2015/0086420 A1 | 3/2015 | Trapani |
| 2015/0129781 A1 | 5/2015 | Kretschmann |
| 2015/0148734 A1 | 5/2015 | Fewkes et al. |
| 2015/0150233 A1 | 6/2015 | Dykstra |
| 2015/0182646 A1 | 7/2015 | Anderson et al. |
| 2015/0219308 A1 | 8/2015 | Dross et al. |
| 2015/0233536 A1 | 8/2015 | Krames et al. |
| 2015/0273093 A1 | 10/2015 | Holub et al. |
| 2016/0000950 A1 | 1/2016 | Won |
| 2016/0000953 A1 | 1/2016 | Bettles et al. |
| 2016/0015840 A1 | 1/2016 | Gordon |
| 2016/0030609 A1 | 2/2016 | Peterson et al. |
| 2016/0030610 A1 | 2/2016 | Peterson et al. |
| 2016/0091172 A1 | 3/2016 | Wu et al. |
| 2016/0114067 A1 | 4/2016 | Dobrinsky et al. |
| 2016/0114186 A1 | 4/2016 | Dobrinsky et al. |
| 2016/0137528 A1 | 5/2016 | Wipprich |
| 2016/0168384 A1 | 6/2016 | Guidolin et al. |
| 2016/0249436 A1 | 8/2016 | Inskeep |
| 2016/0271280 A1 | 9/2016 | Liao et al. |
| 2016/0271281 A1 | 9/2016 | Clynne et al. |
| 2016/0273717 A1 | 9/2016 | Krames et al. |
| 2016/0276550 A1 | 9/2016 | David et al. |
| 2016/0324996 A1 | 11/2016 | Bilenko et al. |
| 2016/0345569 A1 | 12/2016 | Freudenberg et al. |
| 2016/0346565 A1 | 12/2016 | Rhodes et al. |
| 2016/0349179 A1 | 12/2016 | Rochette et al. |
| 2016/0354502 A1 | 12/2016 | Simmons et al. |
| 2016/0366745 A1 | 12/2016 | Hikmet et al. |
| 2016/0375161 A1 | 12/2016 | Hawkins et al. |
| 2016/0375162 A1 | 12/2016 | Marry et al. |
| 2016/0375163 A1 | 12/2016 | Hawkins et al. |
| 2017/0014538 A1 | 1/2017 | Rantala |
| 2017/0030555 A1 | 2/2017 | Lalicki et al. |
| 2017/0081874 A1 | 3/2017 | Daniels |
| 2017/0094960 A1 | 4/2017 | Sasaki et al. |
| 2017/0100494 A1 | 4/2017 | Dobrinsky et al. |
| 2017/0100607 A1 | 4/2017 | Pan et al. |
| 2017/0281812 A1 | 10/2017 | Dobrinsky et al. |
| 2017/0368210 A1 | 12/2017 | David et al. |
| 2018/0043044 A1 | 2/2018 | Hachiya et al. |
| 2018/0113066 A1 | 4/2018 | Freitag et al. |
| 2018/0117189 A1 | 5/2018 | Yadav et al. |
| 2018/0117190 A1 | 5/2018 | Bailey |
| 2018/0117193 A1 | 5/2018 | Yadav et al. |
| 2018/0117194 A1 | 5/2018 | Dobrinsky et al. |
| 2018/0124883 A1 | 5/2018 | Bailey |
| 2018/0139817 A1 | 5/2018 | Yamakawa et al. |
| 2018/0147417 A1 | 5/2018 | Rantala |
| 2018/0180226 A1 | 6/2018 | Van Bommel et al. |
| 2018/0185533 A1 | 7/2018 | Lalicki et al. |
| 2018/0190625 A1 | 7/2018 | Steckel et al. |
| 2018/0280723 A1 | 10/2018 | Enwemeka et al. |
| 2018/0311386 A1 | 11/2018 | Hawkins et al. |
| 2018/0320872 A1 | 11/2018 | Weeks, Jr. et al. |
| 2019/0070323 A1 | 3/2019 | Atreya et al. |
| 2019/0091355 A1* | 3/2019 | Ukawa ............... C09K 11/7774 |
| 2019/0368936 A1 | 12/2019 | Xu et al. |
| 2019/0371978 A1 | 12/2019 | Iwasa et al. |
| 2020/0405893 A1 | 12/2020 | Barron et al. |
| 2021/0030905 A1 | 2/2021 | Barron et al. |
| 2022/0241440 A1 | 8/2022 | Hawkins et al. |

FOREIGN PATENT DOCUMENTS

| | | |
|---|---|---|
| CN | 201423033 Y | 3/2010 |
| CN | 102213382 A | 10/2011 |
| CN | 103227255 A | 7/2013 |
| CN | 105304801 A | 2/2016 |
| CN | 105339094 A | 2/2016 |
| CN | 105449081 A | 3/2016 |
| CN | 205360038 U | 7/2016 |
| CN | 106937461 A | 7/2017 |
| CN | 107575849 A | 1/2018 |

(56) References Cited

FOREIGN PATENT DOCUMENTS

| | | |
|---|---|---|
| DE | 102011001097 A1 | 9/2012 |
| DE | 102015207999 A1 | 11/2016 |
| DE | 102016009175 A1 | 2/2017 |
| EP | 0306301 A1 | 3/1989 |
| EP | 1693016 A1 | 8/2006 |
| EP | 1887298 A1 | 2/2008 |
| EP | 1943880 B1 | 4/2013 |
| FR | 2773715 A1 | 7/1999 |
| JP | 2003-332620 A | 11/2003 |
| JP | 2003339845 A | 12/2003 |
| JP | 2004261595 A | 9/2004 |
| JP | 2004275927 A | 10/2004 |
| JP | 2007511279 A | 5/2007 |
| JP | 2008-004948 A | 1/2008 |
| JP | 2009-004351 A | 1/2009 |
| JP | 2011-513996 A | 4/2011 |
| JP | 2013-045896 A | 3/2013 |
| JP | 2013-093311 A | 5/2013 |
| JP | 2015-015106 A | 1/2015 |
| JP | 2015-035373 A | 2/2015 |
| JP | 2015076527 A | 4/2015 |
| JP | 2015174026 A | 10/2015 |
| KR | 20130096965 A | 9/2013 |
| KR | 101526261 B1 | 6/2015 |
| KR | 20160021100 A | 2/2016 |
| KR | 101648216 B1 | 8/2016 |
| KR | 20160127469 A | 11/2016 |
| KR | 101799538 B1 | 11/2017 |
| TW | M268106 U | 6/2005 |
| TW | 201412240 A | 4/2014 |
| TW | 201604490 A | 2/2016 |
| TW | 201611849 A | 4/2016 |
| TW | M530654 U | 10/2016 |
| TW | 201711707 A | 4/2017 |
| TW | 201831977 A | 9/2018 |
| TW | 201936226 A | 9/2019 |
| WO | 0114012 A1 | 3/2001 |
| WO | 03037504 A1 | 5/2003 |
| WO | 2003035118 A2 | 5/2003 |
| WO | 03063902 A2 | 8/2003 |
| WO | 03084601 A2 | 10/2003 |
| WO | 03089063 A1 | 10/2003 |
| WO | 2004033028 A2 | 4/2004 |
| WO | 2005048811 A2 | 6/2005 |
| WO | 2005049138 A1 | 6/2005 |
| WO | 2006023100 A1 | 3/2006 |
| WO | 2006100303 A2 | 9/2006 |
| WO | 2006126482 A1 | 11/2006 |
| WO | 2007012875 A1 | 2/2007 |
| WO | 2007035907 A2 | 3/2007 |
| WO | 2008071206 A1 | 6/2008 |
| WO | 2009056838 A1 | 5/2009 |
| WO | 2010110652 A1 | 9/2010 |
| WO | 2015066099 A2 | 5/2015 |
| WO | 2015189112 A1 | 12/2015 |
| WO | 2016019029 A1 | 2/2016 |
| WO | 2016068285 A1 | 5/2016 |
| WO | 2016209632 A1 | 12/2016 |
| WO | 2017009534 A1 | 1/2017 |
| WO | 2017205578 A1 | 11/2017 |
| WO | 2019108432 A1 | 6/2019 |

OTHER PUBLICATIONS

Sep. 29, 2020—(WO) ISR & WO—App PCT/US2020/046504.
Absorption and Fluorescence Spectroscopy of Tetraphenylporphyrin§ and Metallo-Tetraphenylporphyrin, article, 2005, 11 pp., Atomic, Molecular and Supramolecular Studies.
Ashkenazi, H. et al., "Eradication of Propionibacterium acnes by its endogenic porphyrins after illumination with high intensity blue light," FEMS Immunology and Medical Microbiology, 35, pp. 17-24, 8 pages.
Ayat M. Ali, Effect of MRSA Irradiation by 632, 532, and 405 nm (Red, Blue, and Green) Diode Lasers on Antibiotic Susceptibility Tests, Article, Jun. 2007, 7 pp, vol. 59, No. 2 , 2017, J Fac Med Baghdad.
Bache et al., "Clinical studies of the High-Intensity Narrow-Spectrum light Environmental Decontamination System (HINS-light EDS), for continuous disinfection in the burn unit inpatient and outpatient settings," Burns 38 (2012), pp. 69-76, 8 pages.
Bek-Thomsen, M., "Acne is Not Associated with Yet-Uncultured Bacteria," J. Clinical Microbial., 2008, 46{10), 9 pages.
Berezow Alex, How to Kill Insects With Visible Light, Real Clear Science, Jan. 11, 2015, pp. 1-4<https://www.realclearscience.com/journal_club/2015/01/12/how_to_kill_insects_with_visible_light_109021.html>, 4 pages.
Burchard, R. et al., "Action Spectrum for Carotenogenesis in Myxococcus xanthus," Journal of Bateriology, 97(3), 1969, pp. 1165-1168, 4 pages.
Burkhart, C. G. et al., "Acne: a review of immunologic and microbiologic factors," Postgraduate Medical Journal, 1999, vol. 75, pp. 328-331, 5 pages.
Burkhart, C. N. et al., "Assessment of etiologic agents in acne pathogenesis," Skinmed, 2003, vol. 2, No. 4, pp. 222-228, 7 pages.
Chukuka et al., Visible 405 nm SLD light photo-destroys metchicillin-resistant *Staphylococcus aureus* {MRSA) in vitro, Lasers in Surgery and Medicine, vol. 40, Issue 10, Dec. 8, 2008, retrieved from: https://onlinelibrary.wiley.com/doi/abs/10.1002/lsm.20724 on Mar. 23, 2018, 4 pages, abstract only provided.
Clauditz, A. et al., "Staphyloxanthin plays a role in the fitness of *Staphylococcus aureus* and its ability to cope with oxidative stress," Infection and Immunity, 2006, vol. 74, No. 8, 7 pages.
Color Phenomena, "CIE-1931 Chromaticity Diagram," last updated Aug. 22, 2013, retrieved from www.color-theory-phenomena.nl/10.02.htm on Jan. 20, 2016, 3 pages.
Dai et al., "Blue light for infectious diseases: Propionibacterium acnes, Helicobacter pylori, and beyond?," Drug Resist Update, 15(4): 223-236 {Aug. 2012), 18 pages.
Dai et al., "Blue Light Rescues Mice from Potentially Fatal Pseudomonas aeruginosa Burn Infection: Efficacy, Safety, and Mechanism of Action," Antimicrobial Agents and Chemotherapy, Mar. 2013, vol. 57{3), pp. 1238-1245, 8 pages.
Dayer, et al., Band Assignment in Hemoglobin Porphyrin Ring Spectrum: Using Four-Orbital Model of Gouterman, article, Sep. 8, 2009, Protein & Peptide Letters, 2010, vol. 17, No. 4, Department of Biology, Faculty of Sciences, Shahid Chamran University of Ahvaz, Tehran, Iran, 7 pages.
Demidova, T. et al., "Photodynamic Therapy Targeted to Pathogens," International Journal of Immunipathology and Pharmacology, 17(3), pp. 245-254, 10 pages.
Dornob, "Healthy Handle: Self-Sanitizing UV Door Knob Kills Germs", Dornob.com, Dec. 5, 2018, pp. 1-6, https://dornob.com/healthy-handle-self-sanitizing-uv-door-knob-kills-germs/, 6 pages.
Drew Prindle, "This UV-Emitting Door Handle Neutralizes Bacteria, Helps Fight the Spread of Disease", Digital Trends, Jun. 19, 2015, https://www.digitaltrends.com/cool-tech/uv-door-handle-kills-germs/, 11 pages.
Elman, M. et al., "The Effective Treatment of Acne Vulgaris by a High-intensity, Narrow Band 405-420 nm Light Source," Cosmetic & Laser Ther, 5, pp. 111-116, 6 pages.
Feng-Chyi Duh et al., "Innovative Design of an Anti-bacterial Shopping Cart Attachment", Journal of Multidisciplinary Engineering Science and Technology (JMEST), Oct. 10, 2015, vol. 2 Issue 10, pp. 2806-2810, http://www.jmest.org/wp-content/uploads/JMESTN42351112.pdf, 5 pages.
Feuerstein et al., "Phototoxic Effect of Visible Light on Porphyromonas gingivalis and Fusobacterium nucleatum: An In Vitro Study," Photochemistry and Photobiology, vol. 80, Issue 3, Apr. 30, 2007, retrieved from: https://onlinelibrary.wiley.com/doi/abs/10.1111/j.1751-1097.2004.tb00106.x on Mar. 23, 2018, abstract only, 4 pages.
Gillespie et al., "Development of an antimicrobial blended white LED system containing pulsed 405nm LEDs for decontamination applications," Progress in Biomedical Optics and Imaging, SPIE—International Society for Optical Engineering, Bellingham, WA, vol. 10056, Mar. 14, 2017, pp. 100560Y-100560Y, XP060084045, whole document.

(56) References Cited

OTHER PUBLICATIONS

Guffey et al., "In Vitro Bactericidal Effects of 405-nm and 470-nm Blue Light," Photomedicine and Laser Surgery, vol. 24, No. 6, retrieved from: https://www.liebertpub.com/doi/abs/10.1089/pho.2006.24.684 on Mar. 23, 2018, abstract only provided, 2 pages.

Halstead et al., "The antibacterial activity of blue light against nosocomial wound pathogens growing planktonically and as mature biofilms," Appl. Environ, Microbial., vol. 82, No. 13, Jul. 2016, pp. 4006-4016, 11 pages, retrieved from: https://aem.asm.org/content/aem/82/13/4006.full.pdf.

Hamblin et al., "Helicobacter pylori Accumulates Photoactive Porphyrins and Is Killed by Visable Light," Antimicrobial Agents and Chemotherapy, Jul. 2005, pp. 2822-2827, 6 pages.

Harrison, A.P., "Survival of Bacteria," Annu. Rev. Microbial, 1967, p. 143, vol. 21, 1 page.

Holzman, "405-nm Light Proves Potent at Decontaminating Bacterial Pathogens," retrieved from: http://forms.asm.org/microbe/index.asp?bid=64254 on Aug. 6, 2015, 34 pages.

Hori Masatoshi et al., Lethal Effects of Short-Wavelength Visible Light on Insects, Scientific Reports, Dec. 9, 2014, pp. 1-6, Graduate School of Agricultural Science, Tohoku University, Sendai, Japan<https://www.semanticscholar.org/paper/Lethal-effects-of-short-wavelength-visible-light-o-Hori-Shibuya/2c11cb3f70a059a051d8ed02fff0e8a9b7a4c4d4>, 6 pages.

Huffman, D. et al., "Inactivation of Bacteria, Virus and Cryptospordium by a Point-of-use Device Using Pulsed Broad Spectrum White Light," Wat. Res. 34(9), pp. 2491-2498, 8 pages.

Jagger, "Photoreactivation and Photoprotection," Photochemistry and Photobiology, vol. 3, Issue 4, Dec. 1964, retrieved from: https://onlinelibrary.wiley.com/doi/abs/10.1111/j.1751-1097.1964.tb08166.x on Mar. 23, 2018, 4 pages, abstract only provided.

Jappe, U., "Pathological mechanisms of acne with special emphasis on Propionibacterium acnes and related therapy," Acta Dermato-Venereologica, 2003, vol. 83, pp. 241-248, 8 pages.

Josefsen, et al., Unique Diagnostic and Therapeutic Roles of Porphyrins and Phthalocyanines in Photodynamic Therapy, Imaging and Theranostics, article, Oct. 4, 2012, 51 pp., 2012; 2(9):916-966. doi: 10.7150/thno.4571, Ivyspring International Publisher, Department of Chemistry, The University of Hull, Kingston-Upon-Hull, HU6 7RX, U.K., 51 pages.

Kawada et al., "Acne Phototherapy with a high-intensity, enhanced, narrow-band, blue light source: an open study and in vitro investigation," Journal of Dermatological Science 30 (2002) pp. 129-135, 7 pages.

Kickstarter, "Orb, The World's First Germ-Killing Blue/UV Light Ball", Dec. 10, 2018, pp. 1-10, <https://www.kickstarter.com/projects/572005089078660/orbtm-the-worlds-first-germ-killing-uv-light-ball>, 10 pages.

Kim, et al., In Vitro Bactericidal Effects of 625, 525, and 425nm Wavelength (Red, Green, and Blue) Light-Emitting Diode Irradiation, article, 2013, 9 pp., vol. 31, No. 11, 2013, Department of Oral Pathology Medical Research Center for Biomineralization Disorders School of Dentistry Dental Science Research Institute, Korea, 9 pages.

Knowles et al., "Near-Ultraviolet Mutagenesis in Superoxide Dismutase-deficient Strains of *Escherichia coli*," Environmental Health Perspectives, vol. 102{1}, Jan. 1994, pp. 88-94, 7 pages.

Kristoff et al., "Loss of photoreversibility for UV mutation in *E. coli* using 405 nm or near-US challenge," Mutat Res., May 1983, 109{2}: 143-153, 2 pages, abstract only provided.

Kundrapu et al. "Daily disinfection of high touch surfaces in isolation rooms to reduce contamination of healthcare workers' hands". Journal of Infection Control and Hospital Epidemiology; vol. 33, No. 10, pp. 1039-1042, published Oct. 2012, 6 pages.

LEDs Magazine, "ANSI continues advancements on SSL chromaticity standard," retrieved from the Internet on Apr. 20, 2017 at: http://www.ledsmagazine.com/articles/print/volume-12/issue-11/features/standards/ansi-continues-advancements-on-ssl-chromaticity-standard.html, Published Dec. 8, 2015, 6 pages.

LEDs Magazine, "ANSI evaluates revisions to SSL chromaticity standard," retrieved from the Internet on Apr. 20, 2017 at: http://www.ledsmagazine.com/articles/2011/07/ansi-evaluates-revisions-to-ssl-chromaticity-standard-magazine.html, Published Jul. 18, 2011, 4 pages.

LEDs Magazine, "ANSI works to update the solid-state lighting standard for chromaticity," retrieved from the Internet on Apr. 20, 2017 at: http://www.ledsmagazine.com/articles/print/volume-12/issue-2/features/standards/ansi-works-to-update-the-ssl-chromaticity-standard.html, Published Feb. 23, 2015, 5 pages.

LEDs Magazine, "Lumination Vio LED combines 405 nm chip with new phosphors," retrieved from the Internet on Apr. 20, 2017 at: http://www.leds.magazine.com/articles/2007/06/lumination-vio-led-combines-405-nm-chip-with-new-phosphors.html, Published Jun. 14, 2007, 2 pages.

Maclean et al., "High-intensity narrow-spectrum light inactivation and wavelength sensitivity of *Staphylococcus auresu*," FEMS Microbial. Lett., vol. 285 (2008) pp. 227-232, 6 pages.

Maclean et al., "Inactivation of Bacterial Pathogens following Exposure to Light from a 405-Nanometer Light-Emitting Diode Array," Applied and Environmental Microbiology, vol. 75, No. 7, Apr. 2009, pp. 1932-1937, 6 pages.

Marshall, J. H., et al., "Pigments of *Staphylococcus au reus*, a series of triterpenoid carotenoids," J. Bacteriology, 1981, vol. 147, No. 3, pp. 900-913, 14 pages.

Master Blaster, Tohoku University Team Discovers Blue Light is Effect at Killing Insects, Sora News 24, Dec. 12, 2014, pp. 1-5, Japan, <https://en.rocketnews24.com/2014/12/12/tohoku-university-team-discovers-blue-light-is-effective-at-killing-insects/>, 5 pages.

Nussbaum, et al., Effects of 630-, 660-, 810-, and 905-nm Laser Irradiation, Delivering Radiant Exposure of 1-50 J/cm2 on Three Species of Bacteria in Vitro, journal, 2002, vol. 20, No. 6, 2002, Journal of Clinical LaserMedicine & Surgery, Canada, 9 pages.

NuTone, "NuTone Bath and Ventilation Fans", Dec. 11, 2018, pp. 1-2, http://www.nutone.com/products/filter/qt-series-fanlights-25a05450-d47b-4ab8-9992-f8c2cd3f7b90, 2 pages.

Nutone, "QTNLEDB LunAura Collection 110 CFM Fan,Light,LED Nightlight, with Tinted Light Panel, ENERGY STAR® Certified Ventilation Fans", Dec. 11, 2018, p. 1, http://www.nutone.com/products/product/a6da75af-8449-4d4d-8195-7011ce977809, 1 page.

Nutone, "ULTRA PRO™ Series Single-Speed Fans and Fan/Lights", Dec. 11, 2018, p. 1, http://www.nutone.com/products/filter/ultra-pro-series-fanlights-eb590f89-dca2-40e7-af39-06e4cccb96ca, 1 page.

Papageorgiou, P. et al., "Phototherapy with Blue (415 nm) and Red (660 nm) Light in the Treatment of Acne Vulgaris," British Journal of Dermatology, 2000, pp. 973-978, 6 pages.

Pelz, A. et al., "Structure and Biosythesis of Staphyloxanthin from *Staphylococcus aureus*," Journal of Biological Chemistry, Sep. 16, 2005, 9 pages.

Pochi, P.E., "Acne: Androgens and microbiology," Drug Dev, Res., 1988, val. 13, 4 pages, abstract only provided.

R.S. Mcdonald et al., "405 nm Light Exposure of Osteoblasts and Inactivation of Bacterial Isolates From Arthroplasty Patients: Potential for New Disinfection Applications?," European Cells and Materials vol. 25, (2013), pp. 204-214., 12 pages.

Reed, "The History of Ultraviolet Germicidal Irradiation for Air Disinfection," Public Health Reports, Jan.-Feb. 2010, vol. 125, 13 pages.

Rita Giovannetti, The Use of Spectrophotometry UV-Vis for the Study of Porphyrins, article, 2012, 23 pp., InTech Europe, Croatia.

Sakai, K., et al., "Search Method for inhibitors of staphyloxanthin production by methicillin-resistant *Staphylococcus aureus*," Biol. Pharm. Bull., 2012, vol. 35, No. 1, pp. 48-53, 6 pages.

Sarah Ward, "LED Retrofit Health ROI? See VitalVio", Poplar Network website, published on Aug. 13, 2014 and retrieved from website: https://www.poplarnetwork.com/news/led-retrofit-health-roi-see-vitalvio, 6 pages.

Sikora, A. et al., "Lethality of visable light for *Escherichia coli*hemH 1 mutants influence of defects in DNA repair," DNA Repair 2, pp. 61-71, 11 pages.

Sofia Pitt and Andy Rothman, "Bright idea aims to minimize hospital-acquired infections", CNBC News website, published on

(56) References Cited

OTHER PUBLICATIONS

Dec. 9, 2014 and retrieved from website: https://www.cnbc.com/2014/12/09/bright-idea-aims-to-minimize-hospital-acquired-infections.html. 5 pages.

Soraa, "PAR30L 18.5W," retrieved from the Internet on Apr. 20, 2017 at: http://wwwv.soraa.com/products, 5 pages.

Soraa, "PAR30L," retrieved from the Internet on Apr. 20, 2017 at: http://www_soraa.com/products/22-PAR30L, 6 pages.

Tomb et al., "Inactivation of Streptomyces phage C31 by 405 nm light," Bacteriophage, 4:3, Jul. 2014, retrieved from: http:/dx.doi.org/10.4161/bact.32129, 7 pages.

Tong, Y. et al., "Solar radiation is shown to select for pigmented bacteria in the ambient outdoor atmosphere," Photochemistry and Photobiology, 1997, val. 65, No. 1, pp. 103-106, 4 pages.

Tong, Y., et al. "Population study of atmospheric bacteria at the Fengtai district of Beijing on two representative days," Aerobiologica, 1993, vol. 9, 1 page, Abstract only provided.

Tsukada et al., "Bactericidal Action of Photo-Irradiated Aqueous Extracts from the Residue of Crushed Grapes from Winemaking," Biocontrol Science, vol. 21, No. 2, (2016), pp. 113-121, retrieved from: https://www.researchgate.net/publication/304628914., 10 pages.

Turner et al., "Comparative Mutagenesis and Interaction Between Near-Ultraviolet (313- to 405-nm) and Far-Ultraviolet 254-nm) Radiation in *Escherichia coli* Strains with Diffeering Repair Capabilities," Journal of Bacteriology, vol. 147, No. 2, Aug. 1981, pp. 410-417, 8 pages.

Wainwright, "Photobacterial activity of phenothiazinium dyes against methicillin-resistant strains of *Staphylococcus aureus*," Oxford University Press Journals, retrieved from: http://dx.doi.org/10.1111/j.1574-6968.1998.tb12908.x on Jul. 23, 2015, 8 pages.

Wang, Shun-Chung, et al.; "High-Power-Factor Electronic Ballast With Intelligent Energy-Saving Control for Ultraviolet Drinking-Waler Treatment Systems"; IEEE Transactions on Industrial Electronics; vol. 55; Issue 1; Dale of Publication Jan. 4, 2008; Publisher IEEE, 4 pages.

Ward, "Experiments on the Action of Light on Bacillus anthracis," 10 pages.

Wilson et al., "Killing of methicillin-resistant *Staphylococcus aureus* by low-power laser light," J. Med, Microbial., vol. 42 (1995), pp. 62-66, 5 pages.

Yoshimura et al., "Antimicrobial effects of phototherapy and photochemotherapy in vivo and in vitro," British Journal of Dermatology, 1996, 135: 528-532, 6 pages.

Yu, J. et al., "Efficient Visible-Light-Induced Photocatalytic Disinfection on Sulfur-Doped Nanocrystalline Titania," Environ. Sic. Technol., 39, 2005, pp. 1175-1179, 5 pages.

Jul. 21, 2021—(TW) Office Action—TW 108148627.
Aug. 31, 2021—(CN) Office Action—CN 201980033309.1.
Sep. 21, 2021—(JP) Office Action—2020-154129.
Oct. 21, 2021—(TW) Office Action—TW 109132488 w/Trn.
Nov. 15, 2021—(CA) Office Action—CA 3095579.
Jun. 28, 2022—(JP) Office Action—App. No. 2020-154129.
May 4, 2010—(WO) IPRP—App PCT/GB2008/003679 (Univ Strathclyde).
Nov. 2, 2015—(WO) WO & ISR—App PCT/US2015/042678.
Dec. 8, 2016—(WO) ISR & WO—App PCT/US2016/036704 (Kenall Manufacturing Company).
Oct. 20, 2016—(WO) ISR & WO—App PCT/US2016/44634.
Jun. 6, 2017—(US) Third Party Submission—U.S. Appl. No. 15/223,134.
Apr. 16, 2018—(WO) ISR & WO—App PCT/US2017/068755.
Apr. 19, 2018—U.S. Non-Final Office Action—U.S. Appl. No. 15/886,366.
Dec. 3, 2018—U.S. Non-Final Office Action—U.S. Appl. No. 15/857,128.
Dec. 3, 2018—U.S. Restriction Requirement—U.S. Appl. No. 15/856,971.
Dec. 12, 2018—U.S. Final Office Action—U.S. Appl. No. 15/886,420.
Jul. 17, 2018—U.S. Final Office Action—U.S. Appl. No. 15/857,128.
Jul. 19, 2018—U.S. Final Office Action—U.S. Appl. No. 15/856,971.
Jun. 29, 2018—(DE) Office Action—App 112016003453.9.
Mar. 6, 2018—(WO) ISR & WO—App PCT/US2017/068749.
May 9, 2018—U.S. Non-Final Office Action—U.S. Appl. No. 15/886,420.
Nov. 1, 2018—U.S. Final Office Action—U.S. Appl. No. 15/886,366.
Nov. 15, 2018—U.S. Non-Final Office Action—U.S. Appl. No. 16/000,690.
Nov. 27, 2018—(JP) Office Action—JP 2018-525520.
Oct. 1, 2018—U.S. Advisory Action—U.S. Appl. No. 15/856,971.
Oct. 1, 2018—U.S. Advisory Action—U.S. Appl. No. 15/857,128.
Sep. 13, 2018—U.S. Non-Final Office Action—U.S. Appl. No. 15/940,127.
Sep. 21, 2018—U.S. Non-Final Office Action—U.S. Appl. No. 16/022,440.
Apr. 15, 2019—(CA) Examiner's Report—App 2,993,825.
Apr. 15, 2019—(CA) Office Action—App 2,993,825.
Dec. 26, 2019—(TW) Office Action and Search Report—App 107143161.
Dec. 27, 2019—(TW) Office Action and Search Report—App 108111242.
Feb. 11, 2019—(WO) ISR—App PCT/US2018/061859.
Feb. 28, 2019—(WO) ISR & WO—App PCT/US2018/061856.
Feb. 28, 2019—(WO) ISR—App PCT/US2018/061843.
Jan. 4, 2019—(TW) Office Action—App 104124977.
Jan. 9, 2019—U.S. Notice of Allowance—U.S. Appl. No. 15/940,127.
Jul. 8, 2019—(WO) ISR & WO—App PCT/US2019/024593.
Nov. 5, 2019—(JP) Final Office Action—JP 2018-525520.
Nov. 20, 2019—(CA) Examiner's Report—App 2,993,825.
Oct. 1, 2019—(KR) Office Action—App 10-2018-7005077—Eng Tran.
Oct. 9, 2019—(CN) Office Action—CN 201680048598.9.
Sep. 6, 2019—(TW) Office Action—App 107143162.
Sep. 20, 2019—(TW) Office Action—App 107143577.
Apr. 3, 2020—(WO) ISR & WO—App PCT/US2019/67444.
Apr. 14, 2020—(TW) 2nd Office Action—App 107143577 (w/translation).
Dec. 2, 2020—(TW) Rejection Decision—App 108111242 (Eng Trans).
Jul. 23, 2020—(TW) Office Action w/TR—TW 108148627.
Jul. 28, 2020—(TW) Office Action 3 w/TR—TW 107143577.
Jul. 6, 2020—(WO) ISR & WO—App PCT/US2019/068799.
Jun. 1, 2020—(GB) Examiner's Report—App GB1802648.4.
Jun. 18, 2020—(WO) IPRP & WO—App PCT/US2018/061859.
Mar. 18, 2020—(WO) ISR & WO—App PCT/US2019/068799.
May 12, 2020—(JP) Final Office Action—JP 2018-525520.
Nov. 23, 2020—(WO) ISR & WO—App PCT/US2020/051254.

* cited by examiner

SINGLE DIODE DISINFECTION

CROSS-REFERENCE TO RELATED APPLICATIONS

This patent is a continuation of U.S. application Ser. No. 17/172,949 filed Feb. 10, 2021, which is a continuation of U.S. application Ser. No. 16/456,537 filed Jun. 28, 2019, now U.S. Pat. No. 10,918,747, which is a continuation of U.S. application Ser. No. 15/886,366, filed Feb. 1, 2018, now U.S. Pat. No. 10,357,582, which is a continuation-in-part of U.S. application Ser. No. 15/223,134, filed Jul. 29, 2016, now U.S. Pat. No. 9,927,097, which claims priority to U.S. Provisional Application Ser. No. 62/198,726, filed Jul. 30, 2015.

TECHNICAL FIELD DISCLOSURE

The present disclosure concerns a light-emitting device capable of emitting light that can be perceived as white or a hue of white, and more particularly, a light-emitting device capable of emitting light that can be perceived as white or a hue of white while simultaneously causing the inactivation of microorganisms.

BACKGROUND OF THE DISCLOSURE

Light-emitting devices are a primary requirement in most indoor occupied environments to provide illumination of the area, of tasks being completed in the area, and of the area's occupants and objects. Lighting technologies range widely for use indoors, from incandescent and halogen bulbs, to fluorescent and light-emitting diode (LED) bulbs and devices, among many other technologies. The primary purpose of these lighting technologies to date is to provide light that can be observed by humans as what is considered "white" light, which can effectively illuminate different colors, textures, and features of objects in a manner pleasing to humans.

While many technologies are commercially used in lighting, LED lighting is growing as a technology to provide efficient, high quality white light illumination at an effective cost point. Some common LEDs for general illumination use a semiconductor junction that is energized to emit blue light and that is combined with a phosphor material, such as cerium-doped yttrium aluminum garnet (YAG:Ce) to convert a portion of that blue light to other wavelengths of light, such as yellow wavelengths. When balanced properly, the combined light emitted from the semiconductor junction and the phosphor material is perceived as white or a hue of white. Blue light-emitting semiconductors are used currently for many reasons, including relatively high efficiency, relatively low cost, and relatively desirable color benefits of the blue light contribution to the overall spectrum of light (as compared to light-emitting semiconductors that emit light of another color).

Some alternative LED technologies use semiconductor junctions that emit UV, near UV, or violet light instead of blue light. A phosphor material is combined to convert a portion of the blue, violet, or UV light to other wavelengths of light and the two components are balanced appropriately to provide white or a hue of white light. Violet LEDs are used less frequently due to typically lower efficiency and cost performance, but have commercially been shown to be able to provide an adequate visual quality of light in some characteristics like the Color Rendering Index (CRI).

With both of these LED technologies, achieving a relatively high luminous efficacy of emitted radiation is balanced against achieving desirable color characteristics (CRI, correlated color temperature (CCT), Gamut, etc.) of the emitted radiation. In other words, the wavelength of combined light emitted from the lighting device is chosen, in relation to the spectral sensitivity of the human eye, to achieve high efficiency, while minimizing the sacrifice of desired color characteristics.

Alternative light sources have been created with additional performance factors in mind that utilize emitted light in different manners. Lighting fixtures and devices for horticulture, health, warmth, and disinfection have been demonstrated. In addition to being tuned for luminous efficacy of radiation, these lighting fixtures and devices are tuned to provide increased outputs of certain regions of radiation to accomplish the additional performance factor.

These lighting fixtures and devices provide a dual or multiple function of lighting through the use of various alternative functions of light such as photochemical, photobiological, radiant energy, and others. Typically, radiant energy outputs are attempted to be optimized for specific regions matching absorption or activation spectrums of the added function. For example, light fixtures and devices for horticulture are attempted to be optimized for emitting light matching absorption or activation spectrums of chlorophyll and other plant based photo-activated mechanisms. Light fixtures and devices for assisting circadian rhythm are attempted to be optimized for emitting light matching absorption or activation spectrums of melatonin.

In these lighting fixtures and devices that emit light for multiple functions, the light emissions can be balanced to achieve an acceptable level of each function. One of the functions can be general illumination (e.g., when the multiple-function lighting fixtures and devices are used in spaces occupied by humans), in which case, achieving a relatively high luminous efficacy of the emitted light is balanced not only against achieving desirable color characteristics of the emitted light, but also of achieving the one or more other functions to an acceptable or desired level.

BRIEF DESCRIPTION OF THE DISCLOSURE

Embodiments of the disclosure disclosed herein may include a device which inactivates microorganisms, the device including a light emitter and at least one light converting material arranged to convert at least a portion of light from the light emitter, wherein any light emitted from the light emitter and the at least a portion of converted light emitted from the at least one light-converting material mixes to form a combined light, the combined light having a proportion of spectral energy measured in an approximately 380 nm to approximately 420 nm wavelength range of greater than approximately 20%.

Embodiments of the disclosure herein may include a device which inactivates microorganisms, the device including a light emitter and at least one light-converting material arranged to be in a direct path of the first light. The light emitter is configured to emit a first light within a range of 380 nm to 420 nm, and the at least one light-converting material is configured to emit a second light in response to the first light being incident on the at least one light-converting material. The first light exiting the device and the second light exiting the device mix to form a combined light, the combined light being white. The at least one light-converting material includes at least one optical brightener which emits light in the wavelength range of 440 nm to 495 nm.

Embodiments of the disclosure disclosed herein may include a light emitting device comprising at least two light emitters, wherein the at least two light emitters are configured to emit light having a same wavelength in the range of 380 nm to 420 nm; each of the at least two light emitters includes a light-converting material arranged to be in a direct path of the light emitted from a given light emitter; each light-converting material being arranged to convert the wavelength of the light emitted from the given light emitter to a wavelength different therefrom; and the light emitted from each of the light-converting materials combines to form white light.

Embodiments of the disclosure herein may include a light emitting device comprising at least two light emitters, wherein the at least two light emitters are configured to emit light having a same wavelength in the range of 380 nm to 420 nm; one or more of the at least two light emitters includes a light-converting material arranged to be in a direct path of the light emitted from a given light emitter; each light-converting material being arranged to convert the wavelength of the light emitted from the given light emitter to a wavelength different therefrom with the exception that the wavelength of light emitted from at least one light emitter is not converted to a wavelength different therefrom; and the light from any light emitter not passing through a light-converting material combines with the light emitted from each of the light-converting materials to form white light.

BRIEF DESCRIPTION OF THE DRAWINGS

These and other features of the disclosure will be more readily understood from the following detailed description of the various aspects of the disclosure taken in conjunction with the accompanying drawings that depict various aspects of the disclosure.

Figure 1:
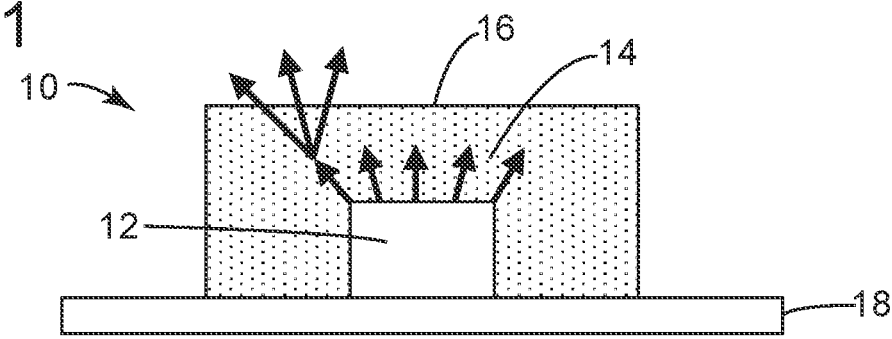
FIG. 1 illustrates a light-emitting device according to various embodiments (the light-emitting device including a light emitter, and a light-converting material contained by an encapsulant).

It is noted that the drawings may not be to scale. The drawings are intended to depict only typical aspects of the disclosure, and therefore should not be considered as limiting the scope of the disclosure. In the drawings, like numbering represents like elements between the drawings. The detailed description explains embodiments of the disclosure, together with advantages and features, by way of example with reference to the drawings.

DETAILED DESCRIPTION OF THE DISCLOSURE

According to various embodiments, a lighting device is disclosed that is capable of emitting light that can be perceived as white or a hue of white and simultaneously is capable of emitting certain concentrations of light with specific wavelengths that are associated with the inactivation of at least some microorganisms.

The light-emitting device is composed of a light emitter (e.g., LEDs, OLEDs, semiconductor dies, lasers), or in some cases two or more light emitters, and one or more light-converting materials (e.g., phosphors, optical brighteners, quantum dots, phosphorescent materials, fluorophores, fluorescent dyes, conductive polymers) assembled in a manner that light emitted from a light emitter will be directed into the light-converting material(s) and at least a portion of this light directed into the light-converting material(s) will be converted by the light-converting material(s) to light having a different quality (e.g., a different peak wavelength). Light can be converted by the light-converting material(s) by absorbing the light, which energizes or activates the light-converting material(s) to emit light of a different quality (e.g., a different peak wavelength). In one embodiment, a combined light emitted by the light emitter(s) and the light-converting material(s) has a proportion of spectral energy measured in an approximately 380 nm to approximately 420 nm wavelength range of greater than approximately 20%. In another embodiment, a combined light emitted by the light emitter(s) and the light-converting material(s) is white and has one or more of the following properties: (a) a proportion of spectral energy measured in an approximately 380 nm to approximately 420 nm wavelength range of greater than approximately 10%, (b) a correlated color temperature (CCT) value of 1000K to 8000K, (c) a color rendering index (CRI) value of 55 to 100, (d) a color fidelity ($R_f$) value of 60 to 100, and (e) a color gamut ($R_g$) value of 60 to 140.

The light emitter(s) and light-converting material(s) may be assembled in many different manners, such as, but not limited to the embodiments depicted in FIGS. 1-15 and 17-20. Light emitted by the light emitter(s) and the light-converting material(s) can be modified by optics, reflectors, or other assembly components to facilitate the combined light emitted by the light-emitting device being perceived as white or a hue of white.

Referring to FIG. 1, a light-emitting device 10 is illustrated that includes a pump LED 12 as the light emitter, a light-converting material 14, an encapsulant 16, and a substrate 18. The light-converting material 104 may be dispersed within encapsulant 106. Pump LED 12 and light-conversion material 104 are supported on the substrate 108.

Figure 2:
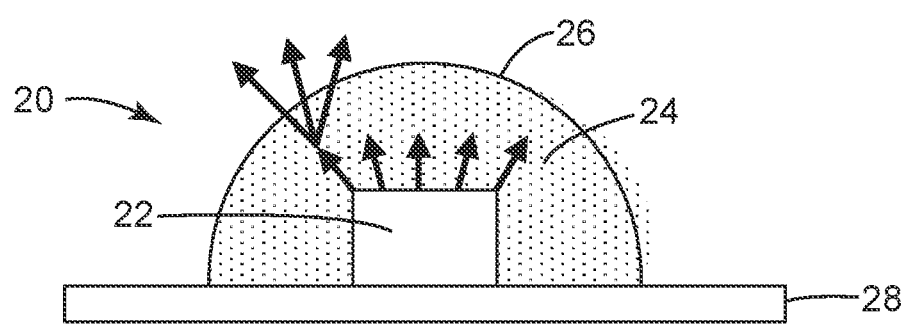
FIG. 2 illustrates another light-emitting device according to various embodiments (the light emitting device including a light emitter, and a light-converting material contained by a lens).

FIG. 2 illustrates a light-emitting device 20 that includes a packaged pump LED 22 as the light emitter, a light-converting material 24, a lens 26 containing the light-converting material 24, and a substrate or base 28.

Figure 3:
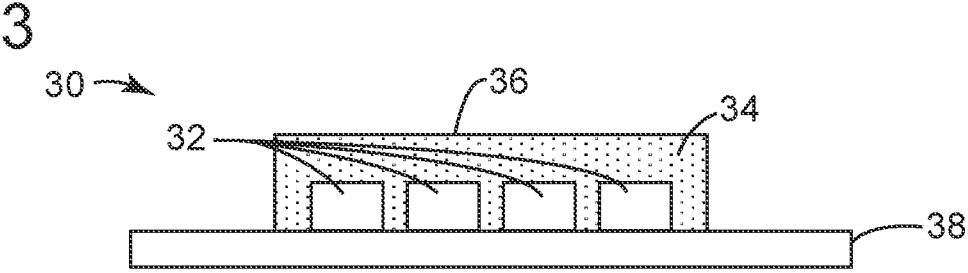
FIG. 3 illustrates another light-emitting device according to various embodiments (the light emitting device including an array of light emitters with a light-converting material thereover).

FIG. 3 illustrates a light-emitting device 30 that includes an array of pump LEDs 32 contained by a light-converting material 34 that is evenly distributed within an encapsulant 36.

Figure 4:
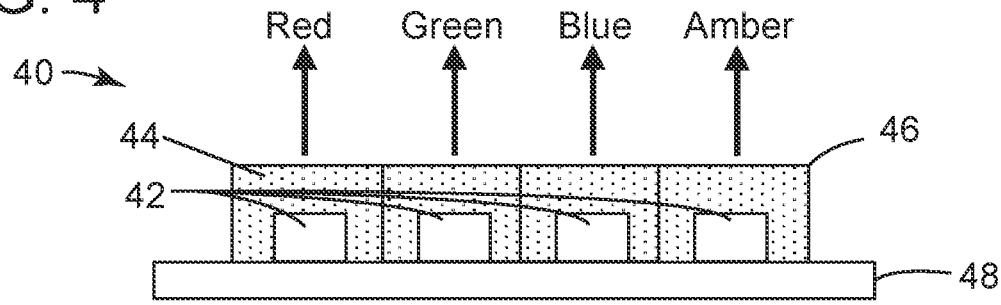
FIG. 4 illustrates another light-emitting device according to various embodiments (the light emitting device including an array of light emitters with a different light-converting material over each light emitter).

FIG. 4 illustrates a light-emitting device 40 that includes an array of LEDs 42 with light-converting materials 44 that convert light to red, green, blue, and amber light. The light-converting materials 44 are shown dispersed, or contained, in an encapsulant 46. LEDs 42 and encapsulant 46 are shown supported on a substrate 48.

Figure 5:
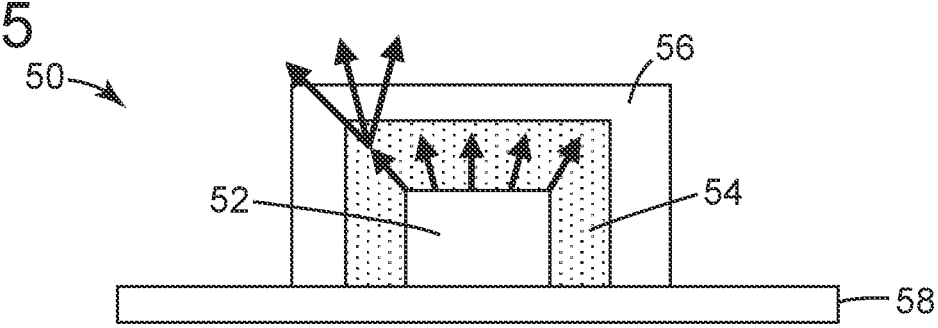
FIG. 5 illustrates another light-emitting device according to various embodiments (the light emitting device including a light emitter and a light-converting material contained by an encapsulant).

FIG. 5 illustrates a light-emitting device 50 that includes LED 52 contained by a light-converting material 54 that is contained by an encapsulant 56, all of which is supported on a substrate 58.

Figure 6:
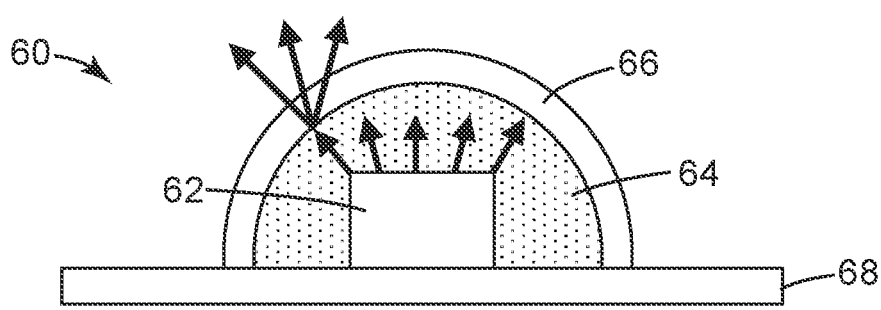
FIG. 6 illustrates another light-emitting device according to various embodiments (the light emitting device including a light emitter and light-converting material contained by a lens).

FIG. 6 illustrates a light-emitting device 60 that includes a packaged LED 62 contained by a light-converting material 64 that is contained by a lens 66. LED 62, light-converting material 64, and lens 66 are supported by a base or substrate 68.

Figure 7:
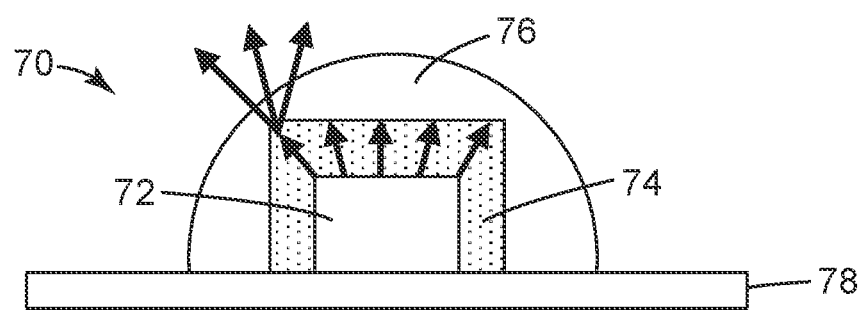
FIG. 7 illustrates another light-emitting device according to various embodiments (the light emitting device including a light emitter and conformal light-converting material contained by a lens).

FIG. 7 illustrates a light-emitting device 70 that includes a packaged LED 72 contained by conformally coated light-converting material 74 that is contained by a lens 76. LED 72, light-converting material 74, and lens 76 are supported on a base or substrate 78.

Figure 8:
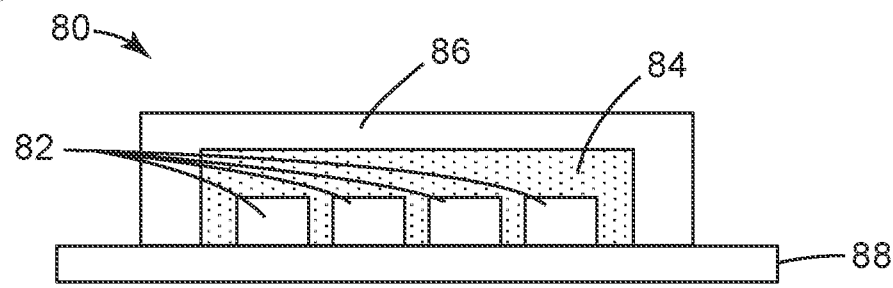
FIG. 8 illustrates another light-emitting device according to various embodiments (the light emitting device including an array of light emitters and a light-converting material contained by an encapsulant).

FIG. 8 illustrates a light-emitting device 80 that includes an array of LEDs 82 contained by a light converting-material 84 that is contained by an encapsulant 86. LEDs 82, light-converting material 84, and encapsulant 86 are supported on a substrate 88.

Figure 9:
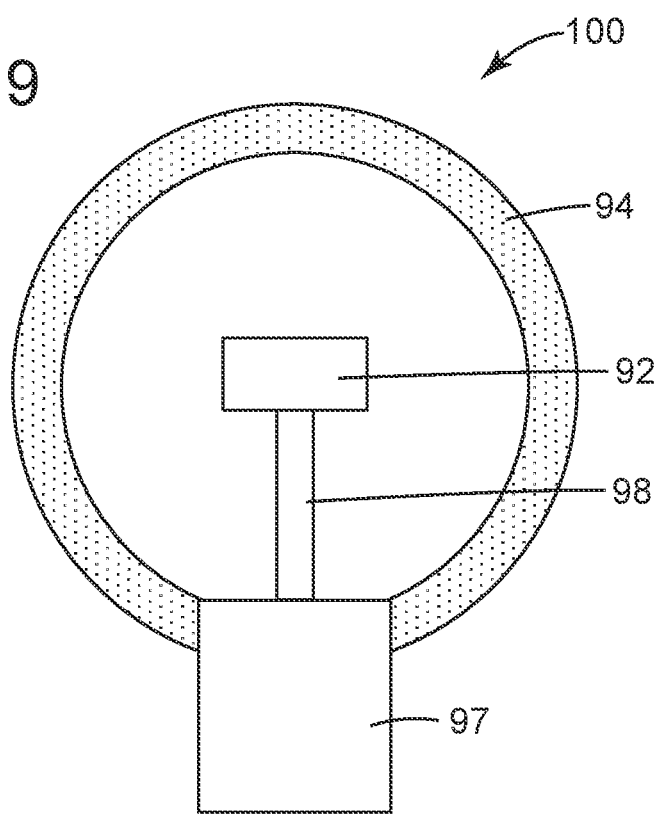
FIG. 9 illustrates another light-emitting device according to various embodiments (the light emitting device being in the form of a light bulb including a light emitter and an outer light-converting filter).

FIG. 9 illustrates a light-emitting device 90 that is a light bulb including LED 92, an outer light-converting filter 94, a base 97, and a pedestal 98. Base 97 and pedestal 98 support LED 92.

Figure 10:
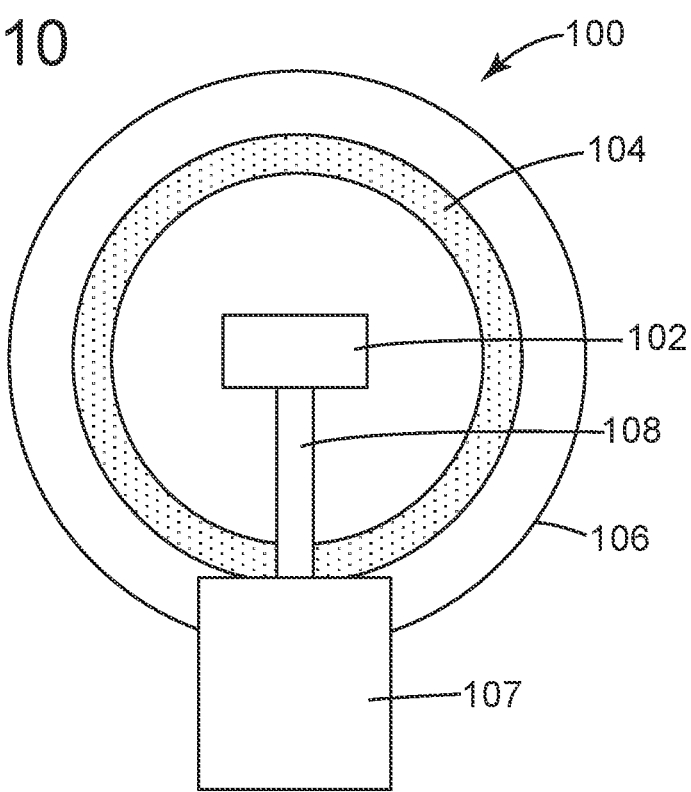
FIG. 10 illustrates another light-emitting device according to various embodiments (the light emitting device being in the form of a light bulb including a light emitter and a light-converting filter contained by an outer bulb).

FIG. 10 illustrates a light-emitting device 100 that is a light bulb including an LED 102, a light-converting filter 104 contained by an outer bulb 106, a base 107, and a pedestal 108. Light-converting filter 104 can directly contact outer bulb 106.

Figure 11:
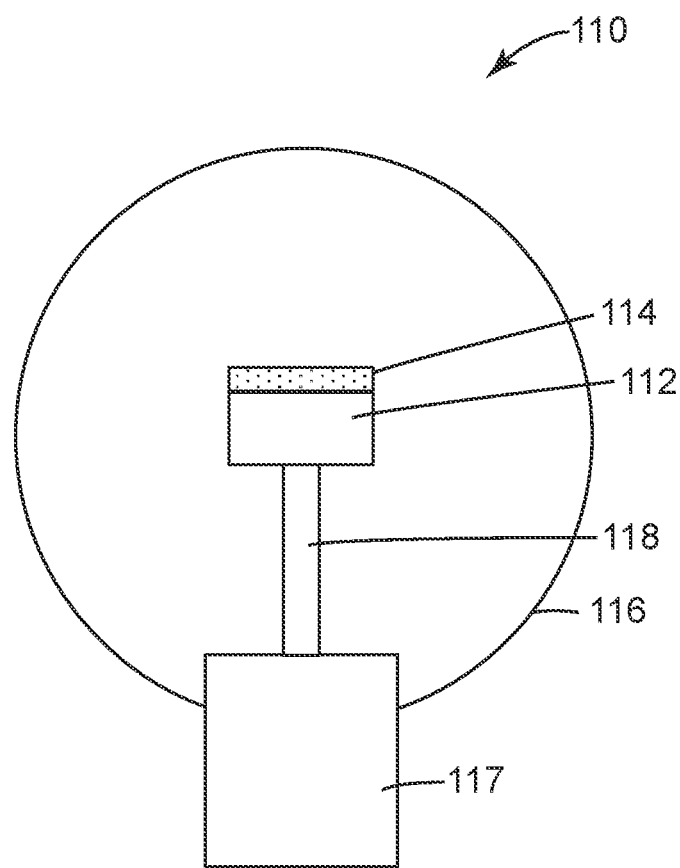
FIG. 11 illustrates another light-emitting device according to various embodiments (the light emitting device being in the form of a light bulb including a light emitter and a light-converting filter on top of the light emitter).

FIG. 11 illustrates a light-emitting device 110 that is a light bulb including an LED 112, a light-converting filter 114 on top of the pump LED 112, an outer bulb 116, a base 117, and a pedestal 118. Light-converting filter 114 can be directly on the pump LED 112.

Figure 12:
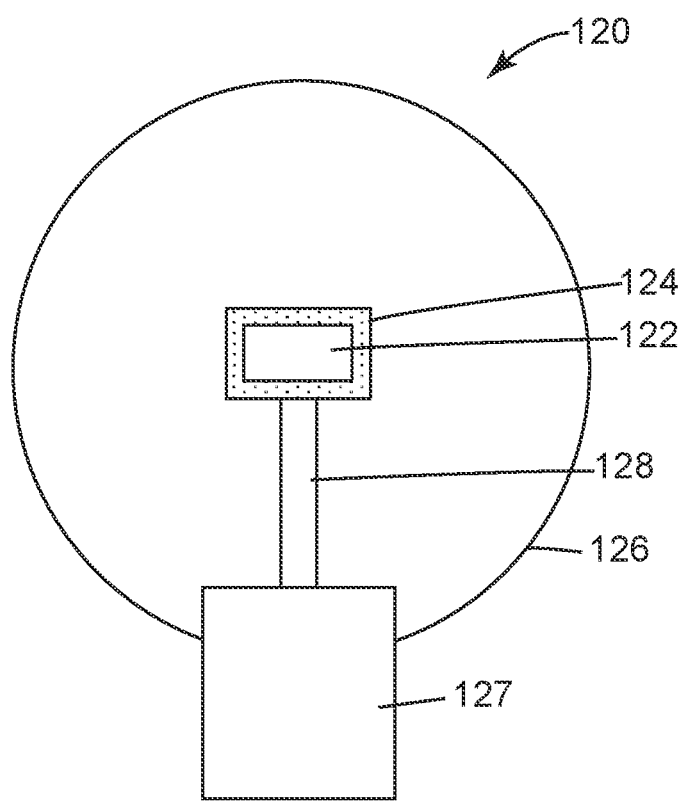
FIG. 12 illustrates another light-emitting device according to various embodiments (the light emitting device being in the form of a light bulb including a light emitter and a light-converting filter surrounding the light emitter).

FIG. 12 illustrates a light-emitting device 120 that is a light bulb including an LED 122, a light-converting filter 124 surrounding the pump LED 122, an outer bulb 126, a base 127, and a pedestal 128. Light-converting filter 124 can directly contact pump LED 122.

Figure 13:
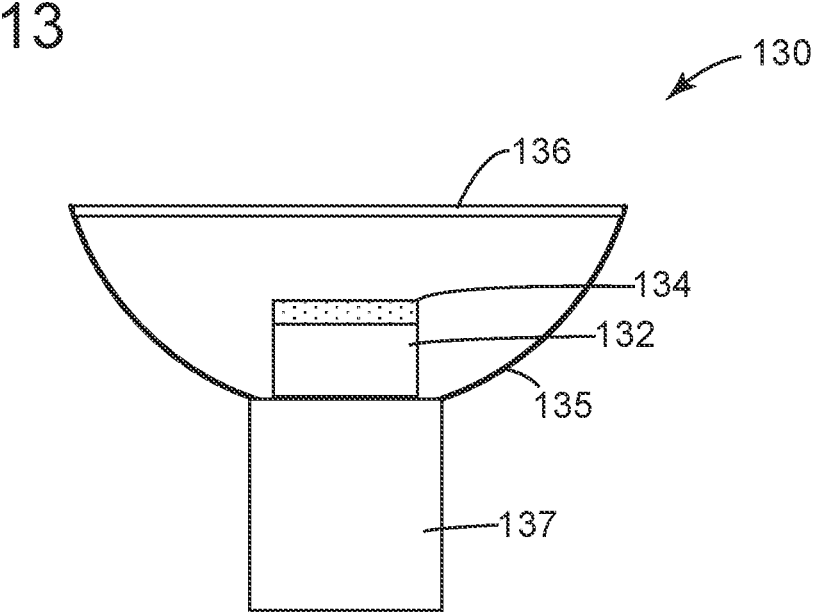
FIG. 13 illustrates another light-emitting device according to various embodiments (the light emitting device being in the form of a spot lamp including a light emitter, a light-converting filter on the light emitter and a lens).

FIG. 13 illustrates a light-emitting device 130 that is a spot lamp including an LED 132, a light-converting filter 134 on pump LED 132, a reflector 135, a lens 136, and a base 137. Light-converting filter 134 can be directly on pump LED 132.

Figure 14:
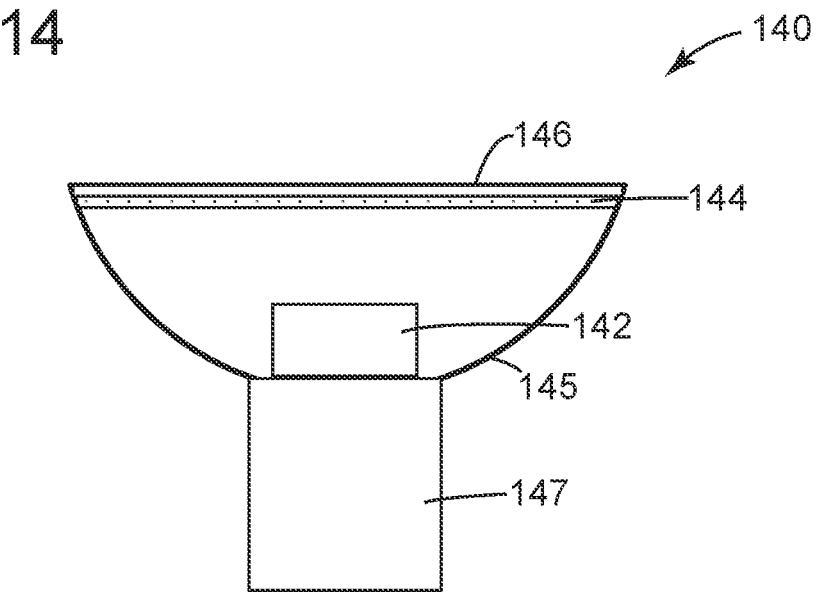
FIG. 14 illustrates another light-emitting device according to various embodiments (the light emitting device being in the form of a spot lamp including a light emitter, a light-converting filter not in contact with the light emitter but in contact with a lens).

FIG. 14 illustrates a light-emitting device 140 that is a spot lamp including, an LED 142, a light-converting filter 144, a reflector 145, a lens 146 on light-converting filter 144, and a base 147. Lens 146 can be directly on light-converting filter 144.

Figure 15:
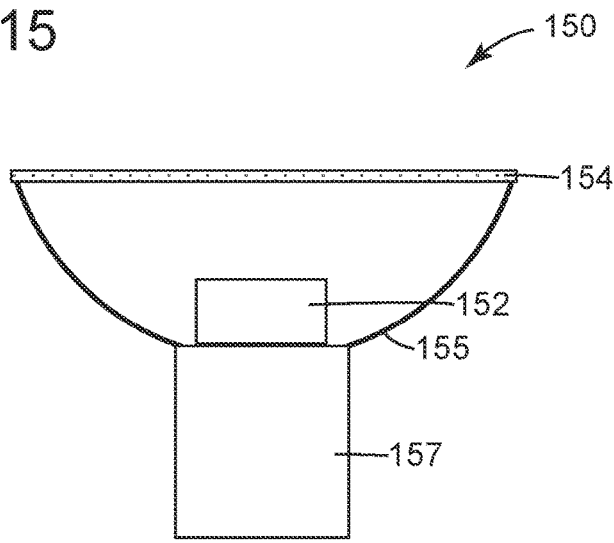
FIG. 15 illustrates another light-emitting device according to various embodiments (the light emitting device being in the form of a spot lamp including a light emitter and a light-converting filter not in contact with the light emitter).

FIG. 15 illustrates a light-emitting device 150 that is a spot lamp including an LED 152, a light-converting filter 154, a reflector 155, and a base 157.

Figure 16:
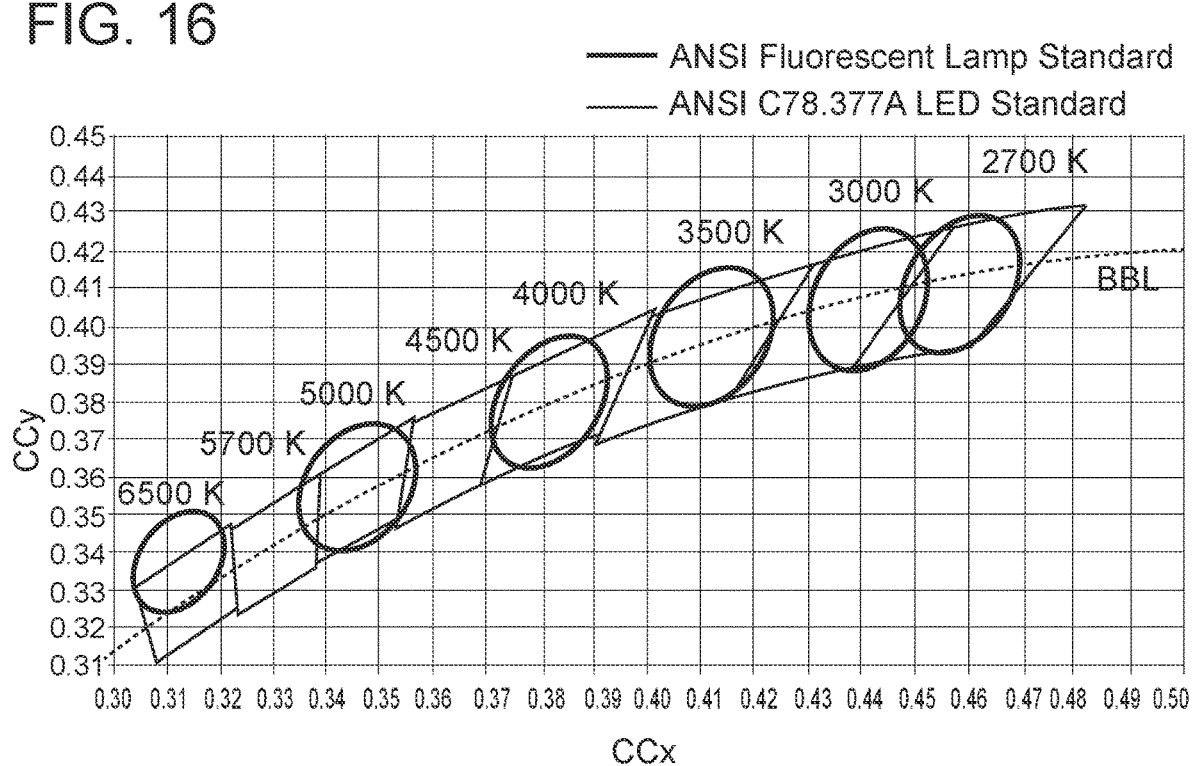
FIG. 16 illustrates an ANSI C78.377A LED standards with accepted x,y coordinates at selected CCTs that are color coordinate ranges for light-emitting devices in some embodiments of the disclosure.

FIG. 16 serves as an example of color coordinates and ranges of color coordinates that could be achieved in practice in some embodiments of the disclosure. More specifically, FIG. 16 illustrates an ANSI C78.377A LED Standards with accepted x-y coordinates at selected CCTs.

Figure 17:
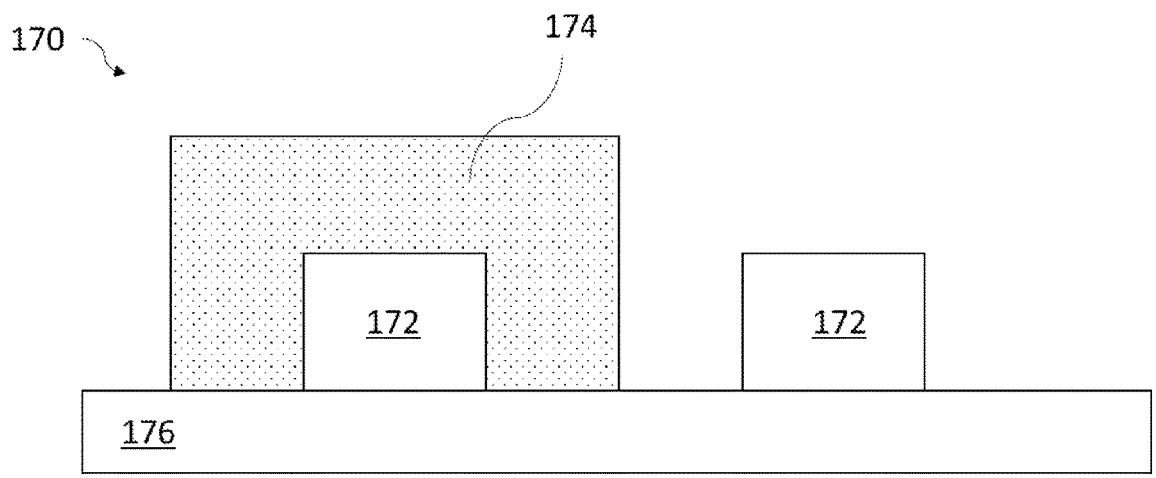
FIG. 17 illustrates a light-emitting device having all violet light emitters wherein at least one of the emitters remains uncovered by a light-converting material.

FIG. 17 illustrates a light-emitting device 170 that includes two light emitters 172, a light-converting material 174, and a substrate 176. Light emitters 172 and light-conversion material 174 are supported on substrate 176. While only two light emitters 172 are shown in FIG. 17, there may be three, four, five, etc. light emitters 172 present in light-emitting device 170. In the embodiment of FIG. 17, all light emitters 172 emit light having a same wavelength, for instance a same wavelength in the range of 380 nm to 420 nm. As shown in FIG. 17, one light emitter 172 includes light-converting material 174 arranged to be in a direct path of the light emitted from light emitter 172 thereunder, while the other light emitter 172 remains uncovered by a light-converting material 174. Any number of light emitters 172 present in light-emitting device 170 may include a light-converting material 174 thereover.

Figure 18:
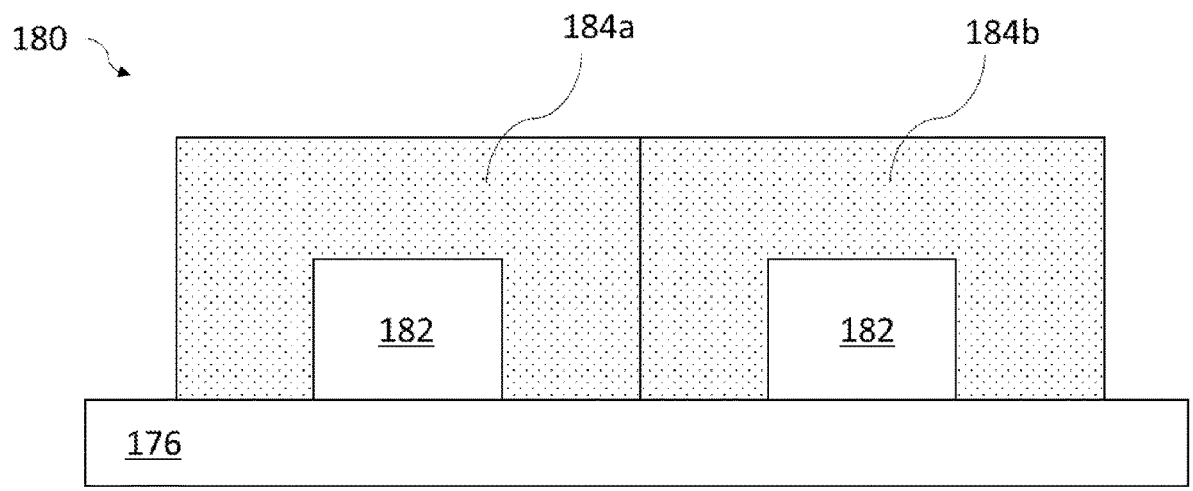
FIG. 18 illustrates another light-emitting device having all violet light emitters wherein all of the emitters have a light-converting material arranged thereover.

FIG. 18 illustrates a light-emitting device 180 that includes two light emitters 182, light-converting materials 184*a* and 184*b*, and substrate 176. The embodiment of FIG. 18 differs from FIG. 17 in that all of light emitters 182 present in light-emitting device 180 include a light-converting material 184 thereover. As also illustrated in FIG. 18, while light emitters 182 are the same, each light emitter 182 has a unique light-converting material 184 thereover, for instance light-converting material 184*a* over a first light emitter 182 and light-converting material 184*b* over a second light emitter 182, and so on. The different light-converting materials capable of use in embodiments of the disclosure are described below.

Figure 19:
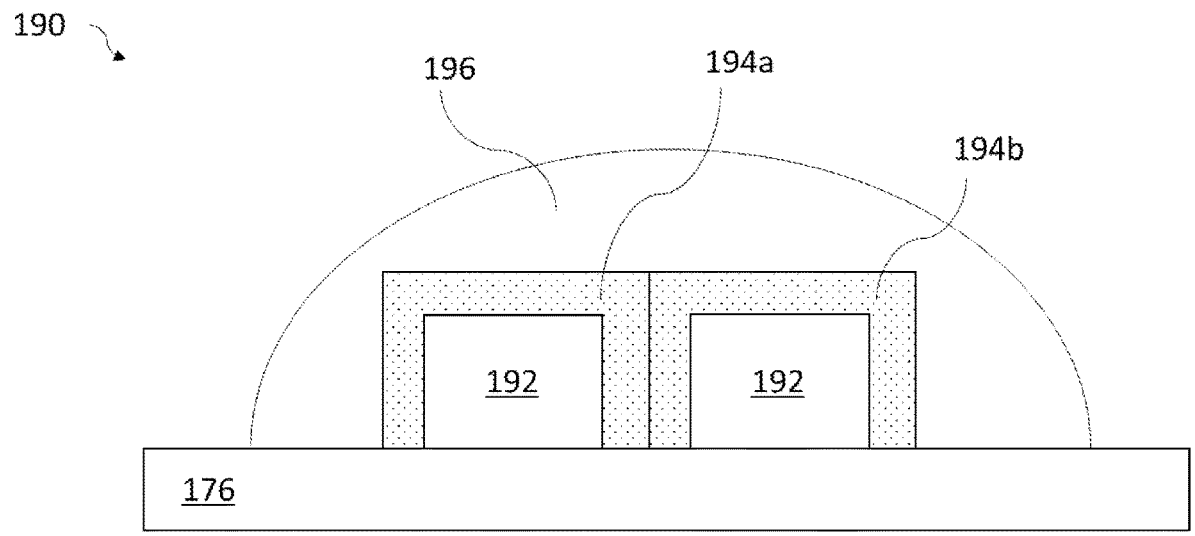
FIG. 19 illustrates another light-emitting device, similar to that of FIG. 18 but with a lens containing the light-converting material.

FIG. 19 illustrates a light-emitting device 190 like that of FIG. 18 with the addition of a lens 196 containing light-converting materials 194*a* and 194*b* and light emitters 192.

Figure 20:
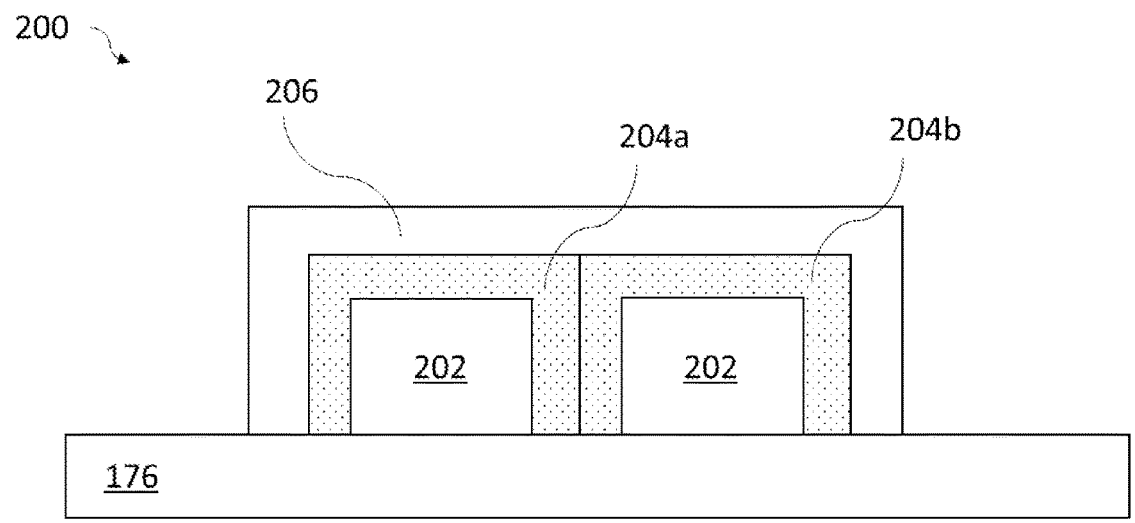
FIG. 20 illustrates another light-emitting device, similar to that of FIG. 18 but with an encapsulant containing the light-converting material.

FIG. 20 illustrates a light-emitting device 200 like that of FIG. 18 with the addition of an encapsulant 206 containing light-converting materials 204*a* and 204*b* and light emitters 202.

Figure 21:
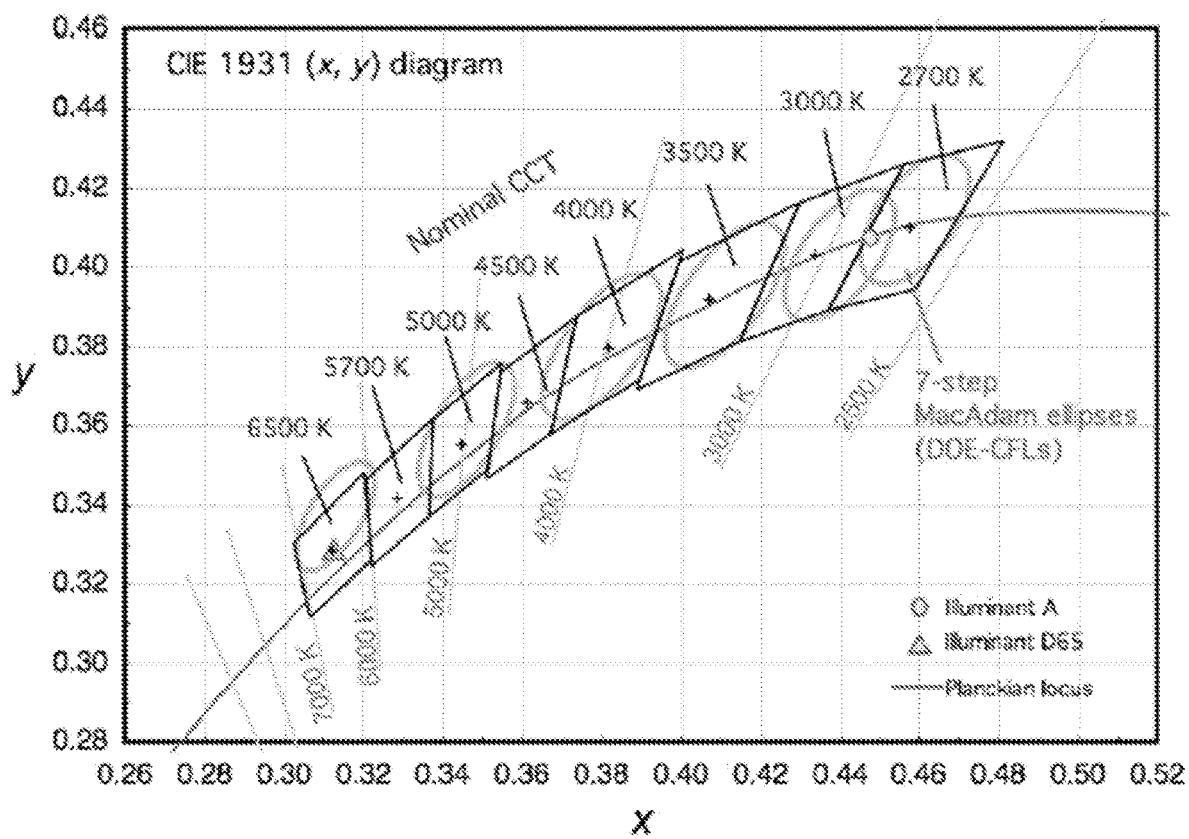
FIG. 21 illustrates an ANSI C78.377-2017 white light standards with accepted x-y coordinates at selected CCTs that are color coordinate ranges for light-emitting devices in some embodiments of the disclosure.

FIG. 21 illustrates ANSI C78.377-2017 white light standards with accepted x,y coordinates at selected CCTs, including 7-step MacAdam ellipses, and that shows quadrangles at various color temperatures for light-emitting devices in some embodiments of the disclosure. The ANSI C78.377-2017 standard states: "The purposes of this standard are, first, to specify the range of chromaticities recommended for general lighting with solid-state lighting products to ensure high-quality white light and, second, to categorize chromaticities with given tolerances so that the white light chromaticity of the products can be communicated to consumers." Thus, the noted ANSI standard tries to define a chromaticity range (defined as "4-step" or "7-step" Quadrangles in the CIE 1931 x,y diagram, or the CIE 1976 u'v' diagram) for high quality white lights at different CCT values. The quadrangles set color consistency bounds so that LED to LED, or even fixture to fixture, lights look consistent. The 4-step or 7-step Quadrangles also help establish how far away from a particular CCT a light can be and still be considered that particular nominal CCT. The device disclosed enables a disinfecting white light that can fall within the bounds of the Quadrangles at various color temperatures through the precise combination of selected emitters and light converting materials as described in embodiments of this disclosure. More specifically, the combined white light emitted from a light emitting device of the present disclosure can be quantified using (x,y) coordinates falling on the CIE 1931 Chromaticity diagram. The color temperature of the combined white light can vary between 1000K to 8000K for different embodiments. The (x,y) coordinates can be determined from a measured Spectral Power Distribution (SPD) graph of the emitted white light spectrum. When graphed, these determined (x,y) coordinates will fall within the bounds of a quadrangle for the color temperature of each embodiment, and thus the combined light emitted can be defined as white light using the ANSI C78.377-2017 standard.

Though illustrated in FIGS. 1-15 as an LED, the light emitter of FIGS. 1-15 as well as FIGS. 17-20 can be any known emitter, including but not limited to a substrate and an LED (e.g., pump LED), a packaged LED, an array of LEDs, an organic LED (OLED), a spot lamp, a laser, a semiconductor die and traditional light bulbs either with an LED replacement fixture or other light bulbs. Each LED can include one or more semiconductor dies that are emitters within an LED package. The light emitter can have a peak wavelength/majority of light output in the 380-420 nm wavelength range of light.

In embodiments with multiple light emitters (e.g., an array of LEDs), the light emitters can all emit light of approximately the same wavelength. For example, the array of LEDs 32 shown in FIG. 3, the array of LEDs 42 shown in FIG. 4, the light emitters 172 shown in FIG. 17, the light emitters 182 shown in FIG. 18, the light emitters 192 shown in FIG. 19 and the light emitters 202 shown in FIG. 20 can all emit light within the range of 380-420 nm. In some embodiments, the array of LEDs 32, 42 and the light emitters 172, 182, 192, 202 can all emit light within the wavelength range of 390-415 nm, and in other embodiments 400 nm-410 nm.

Light-converting material, as used herein, constitutes a broad category of materials, substances, or structures that have the capability of absorbing a certain wavelength of light and re-emitting it as another wavelength of light. Light-converting materials should be noted to be different from light-emitting materials and light-transmitting/filtering materials. Light-emitting materials can be broadly classified as materials, substances, or structures/devices that convert a non UV-VIS-IR form of energy into a UV-VIS-IR light emission. Non ultraviolet-visible-infrared (UV-VIS-IR) forms of energy may be, and are not limited to: electricity, chemical reactions/potentials, microwaves, electron beams, and radioactive decay. Light-converting materials may be contained in or deposited on a medium, making a light-converting medium. It should be understood that light-converting materials, light-converting mediums, light-converting filters, phosphors, and any other terms regarding the conversion of light are meant to be examples of the light-converting material disclosed.

In some embodiments, the light-converting material can be a phosphor, an optical brightener, a combination of phosphors, a combination of optical brighteners, or a combination of phosphor(s) and optical brightener(s). In some embodiments, the light-converting material can be quantum dots, a phosphorescent material, a fluorophore, a fluorescent dye, a conductive polymer, or a combination of any one or more types of light-converting materials. Optical brighteners are light-converting materials (e.g., chemical compounds) that absorb light in the ultraviolet and/or violet regions of the electromagnetic spectrum, and re-emit light in the blue region. Quantum dots are nanometer sized semiconductor particles that can emit light of one or more specific wavelengths when electricity or light is applied to them. The light emitted by quantum dots can be precisely tuned by changing the size, shape and/or material of the quantum dots. Quantum dots can have varying composition and structures that allow them to be classified into different types such as core-type quantum dots, core-shell quantum dots, and alloyed quantum dots. Core-type quantum dots are single component materials with uniform internal compositions, for example chalcogenides (selenides, sulfides or tellurides) of metals like cadmium, lead or zinc (e.g., CdTe or PbS). The photo—and electroluminescence properties of core—type quantum dots can be fine-tuned by changing the crystallite size. Core shell quantum dots have small regions of a first material (core) surrounded by a second material having a wider band gap than the first material (shell) and typically offer improved quantum yield; for example, a CdSe core surrounded by a ZnS shell exhibits greater than 50% quantum yield. Alloyed quantum dots include both homogeneous and gradient internal structures and allow for tuning of both optical and electronic properties by changing the composition and internal structure without changing the crystallite size; for example, alloyed quantum dots of the composition $CdS_xSe_{1-x}/ZnS$ (with 6 nm diameter) can emit light of different wavelengths by adjusting the composition. Light-converting materials can be capable of absorbing multiple different wavelengths of light and emitting multiple different wavelengths of light, in both scaled and not specifically scaled manners.

The phosphor or other light converting material may be deposited directly on the light emitter, as illustrated in at least FIGS. 1-8 and 17-20, or may be remote or further removed from the light emitter, as illustrated in at least FIGS. 9-10 and 14-15, which show a light-converting filter distanced from the light emitter. The remote phosphor configuration reduces flux density through the light-converting filter by increasing surface area of the flux. The physical separation of the light emitter and the light-converting filter, and the reduced flux can reduce the operating temperature of the light-converting filter by reducing conducted heat from the light emitter. The lower temperature of the light-converting filter reduces thermal quenching of the light output and other undesirable effects of elevated operating temperature. Light-converting materials can be deposited, for example, as conformal coatings, doped encapsulants or binder materials, and remote phosphors. The at least one light-converting material may be fully homogenized at different or identical ratios and used as a bulk mix, or the at least one light-converting materials may have some or all portions positioned or layered separately, affecting the absorption and emission of different materials that may not be compatible when mixed or that may absorb too much underlying light.

As mentioned above, the light emitter of the disclosure can include a light-converting material arranged to be in a direct path of the light emitted from a given light emitter. In other words, each light emitter can have its own independent light-converting material arranged to be in a direct path of the light emitted therefrom. This allows for independent selection of light-converting material coverage for each and every light emitter.

In some embodiments, the CRI value of the combined light output or combined emitted light from the light-emitting device (e.g., light emitted from the light emitter mixed with light emitted from the light-conversion material) can have a CRI value of at least 55, 60, 65, or 70. In further embodiments, the CRI value can be at least 80, 85, 90, or 95, plus or minus approximately 5 (allowing for a CRI value of 100).

In some embodiments, the combined light output or combined emitted light from the light-emitting device can be white light. White light can be defined as light with a correlated color temperature (CCT) value of approximately 1000 kelvin (K) to approximately 8000K, in some embodiments approximately 2000K to approximately 6000K, and in some embodiments approximately 2500K to approximately 5000K, wherein "approximately" can include plus or minus about 200K.

White light can also be defined according to a variety of other industry standards such as but not limited to: the ANSI C78.377-2017 white light standard, described above, the Fidelity Index ($R_f$) which provides a color fidelity value, and the Gamut Index ($R_g$) which provides a color gamut value. Sometimes $R_f$ and $R_g$ values are reported in combination as the "TM-30-15" standard. $R_f$ represents how closely the color appearances of an entire sample set are reproduced (rendered) on average by a test light as compared to those under a reference illuminant. Thus, $R_f$ combines the computed color differences for all test-color samples in one single average index value, and is only one aspect of color quality not considering perception/preference effects. $R_g$ provides information about the relative range of colors that can be produced (via reflection) by a white light source. A score close to 100 indicates that, on average, the light source reproduces colors with similar levels of saturation as an incandescent bulb (2700K) or daylight (5600K/6500K).

In some embodiments, the light-emitting device can have a spectral content of light output in the 380-420 nm wavelength range of at least 10%. The spectral content of light output in the 380-420 nm wavelength range is defined as the proportion of absolute irradiance value of light having wavelengths in the range of 380-420 nm relative to the absolute irradiance value of light having wavelengths in the range of 380-720 nm. Dividing the former value by the latter value yields the % spectral content of emitted light in the 380-420 nm wavelength range. The spectral output is defined as the radiometric energy. The absolute irradiance values can be measured by any now-known or later-developed means. In some embodiments, the absolute irradiance values are measured in mW of radiometric energy.

The spectral content in the 380-420 nm wavelength range can be utilized for the inactivation of bacterial pathogens. A 405 nm peak wavelength and a range of wavelengths above and below 405 nm (380-420 nm) have proven effective for the inactivation of bacterial pathogens.

As one example, the device may be assembled similarly to a "blue-phosphor" LED device. A blue-phosphor LED device is a single package electronic device capable of emitting light. The embodiment of the device depicted in FIG. 2, as well as several of the other figures, for example, could be architecturally similar to a "blue-phosphor" LED device. Typically, in a "blue-phosphor" LED device, a semiconductor LED capable of emitting blue light is covered or surrounded by a phosphor material or otherwise placed so that light emitted from the diode passes though the phosphor. The "blue-phosphor" LED device emits some portion of the original blue light from the LED, and some of the light from the phosphor which has been converted from blue light. The "blue-phosphor" LED device has a combined light emission ratio of the blue light and the light emitted from the phosphor to emit a light that is overall perceived as white.

In some embodiments of the disclosure, 10% or less blue light (440 nm-495 nm) is emitted within the entire emitted spectral energy of the light emitting devices of the disclosure. In some instances, below 7% blue light is emitted by the light emitting devices of the disclosure. This is a low value compared to a conventional blue pumped LED which typically contains 15-20% blue light emitted within the entire emitted spectral energy. Such low blue light content as emitted by the light emitting devices of the disclosure allows for minimal suppression of melatonin in humans which contributes to better sleep, improved behavior, and mood. Thus, the light emitting devices according to the disclosure can be used for circadian rhythm effects.

The LED device according to embodiments of the disclosure is assembled similarly to a "blue-phosphor" LED device but includes a semiconductor LED that emits a majority of light/peak of light within the 380-420 nm wavelength range rather than wavelengths within the conventional range of approximately 440-495 nm, which would be perceived as blue. Light in the 380-420 nm wavelength is capable of killing or deactivating microorganisms such as but not limited to Gram positive bacteria, Gram negative bacteria, bacterial endospores, mold and yeast and filamentous fungi. Some Gram positive bacteria that can be killed or deactivated include *Staphylococcus aureus* (incl. MRSA), *Clostridium perfringens, Clostridium difficile, Enterococcus faecalis, Staphylococcus epidermidis, Staphyloccocus hyicus, Streptococcus pyogenes, Listeria monocytogenes, Bacillus cereus, Mycobacterium terrae, Lactococcus lactis, Lactobacillus plantarum, Bacillus circulans* and *Streptococcus thermophilus*. Some Gram negative bacteria include *Acinetobacter baumannii, Pseudomonas aeruginosa, Klebsiella pneumoniae, Proteus vulgaris, Escherichia coli, Salmonella enteritidis, Shigella sonnei, Serratia* spp. and *Salmonella typhimurium*. Some bacterial endospores include *Bacillus cereus* and *Clostridium difficile*. Some yeast and filamentous fungi include *Aspergillus niger, Candida albicans*, and *Saccharomyces cerevisiae*. Light in the 380-420 nm wavelength has been effective against every type of bacteria tested, although it takes different amounts of time or dosages dependent on species. Based on known results it is expected to be effective against all gram-negative and gram-positive bacteria to some extent over a period of time. It can also be effective against many varieties of fungi, although these will take longer to show an effect.

To kill or deactivate microorganisms on a target surface, a certain intensity of light from a lighting device/fixture is typically required. In some embodiments of the disclosure, a light emitting device emitting light with an intensity of at least 0.01 mW/cm$^2$ (in the 380-420 nm range) on the target surface is attained.

The LED, according to embodiments of the disclosure, or the light emitter(s), according to other embodiments of the disclosure, are surrounded by a phosphor material capable of absorbing and converting some portion of that anti-microbial light emitted from the LED or light emitter(s) (380-420 nm) to an alternative wavelength or wavelengths. This LED or other light emitter(s)-containing device can have a combination of selected phosphors, such as but not limited to Lutetium Aluminum Garnet and Nitride, that when combined at the proper ratios can emit a light perceived as white or a hue of white. This example LED or other light emitter(s)-containing device can have a CRI equal to or greater than 70. In some embodiments, this example LED device can have a CRI equal to or greater than 80. A percentage of spectral content of light emitted from the example LED device with approximately 380-420 nm wavelength can be equal to or greater than 10%. In some embodiments, light with wavelengths in the range from approximately 380-420 nm may comprise at least approximately 20%, 25%, 30%, 35%, 40%, 45%, or 50% of the total combined light emitted from the example LED device.

In some embodiments, the light-emitting device can be a surface mount LED device, which includes an LED and a light-conversion material. The surface mount LED device can be mounted onto a printed circuit board ("PCB") or otherwise configured to be capable of transferring power to the light-emitting device and to the LED. The LED can be coupled to the PCB through bond wires or leads which enable an electrical connection from the LED to the outside of the device. The device may have a lens, encapsulant, or other protective cover. The embodiments shown in FIGS. 1-8 and FIGS. 17-20 can be embodied as surface mount LED devices by arranging them with wires or leads connected to the respective LEDs and configured to be connected to a PCB.

In additional embodiments, the light-emitting device can be a through-hole LED device, which is similar to a surface mount package but is intended to be mounted to a PCB board or otherwise configured to be capable of transferring power into the device and the light emitter via conductive legs which mate with matched holes or vias on the PCB or similar structure. The legs are coupled to the PCB or similar structure through solder or another conductive medium.

In some embodiments, the light-emitting device can be a chip-on-board LED arrangement, which is a package with one or more light sources and a light converting-material. The one or more light sources can be mounted directly to a substrate, and the light-converting material can be placed so a desired portion of emitted light is converted by the light converting material.

In another embodiment, the light-emitting device can be a chip scale package (CSP) or a flip chip CSP, both of which packages the emitters without using a traditional ceramic/plastic package and/or bond wires, allowing the substrate to be attached directly to the printed circuit board.

Unlike previous attempts with devices to produce acceptable light spectrums, which required multiple different light emitters to be incorporated into a device to achieve white light of acceptable characteristics, embodiments of the disclosure do not require multiple different light emitters, which would each require its emitted light to be combined through optics or housing structures, which in turn would require increased electronics, controls, optics, and housing structures. The additional features and increased cost metrics associated with multiple-light-emitter light-emitting devices make color mixing methods inherently cumbersome for these light-emitting devices as compared to light-emitting devices with single light emitters, which can produce a combined light spectrum out of a single assembly.

As mentioned above, typical multiple light emitter devices require the emitted light to be combined/mixed in an optical chamber (by way of, e.g., optics or housing structures). While some embodiments of the disclosure do not require multiple different emitters (i.e., one/single light emitter devices), other embodiments of the disclosure can include multiple-light-emitter light-emitting devices and such multiple light emitter devices of the disclosure do not combine/mix the emitted light in an optical chamber. Multiple light emitter devices of the disclosure are configured such that the emitted light is combined/mixed before it exits a given LED package and thus does not require combining/mixing in the optical chamber.

In one embodiment, a device is disclosed which comprises a unit that uses only violet LEDs (approximately 405 nm) to create white light (see e.g., FIG. 17 through FIG. 20), while maintaining the disinfection capabilities of the desired spectrum. Color temperatures of 2700k, 3500k, and 4100k, with CRI above 80 are possible with a single light emitter (e.g., LED) according to embodiments of the disclosure. Generally, a CCT range of 2700-5000k with minimum CRI of 70, and violet spectral content above 10% is possible. In some embodiments, the use of two or more light-converting materials can achieve these values. In some embodiments, phosphors that convert light to each of red (620-750 nm), green (495-570 nm), and blue (440-495 nm) wavelengths can be used, such as Nitride, Lutetium Aluminum Garnet, and $Ca_2PO_4Cl:Eu^{2+}$, respectively.

A difficult aspect to overcome is a lack of blue light emission in contrast to conventional LED white lights. While violet light can be combined with other colors to create white, it has been found that differences in perception from person to person exist for violet light. This means different people see a combined light differently; some might see too much violet, while others might see not enough violet; causing a misrepresentation of the color of white light overall. In addition, without enough blue light it is more difficult to achieve a high CRI. Previous attempts have utilized blue LEDs mixed with the other colors to boost CRI and balance the color of the mixed light output. Even with this approach some people still see the light differently depending on their sensitivity, but it has shown reduced differentiation of observed color overall of combined spectrums. Some embodiments herein instead add blue light through the use of phosphors, optical brighteners, or other blue emitting materials. These materials can absorb violet light and emit blue light, without the use of a discrete blue LED.

Some phosphor material compositions include aluminate phosphors (e.g., calcium aluminate, strontium aluminate, yttrium aluminate), silicate phosphors, garnet phosphors, nitride phosphors, oxynitride phosphors, Calcium Sulfide, $Ca_2PO_4Cl:Eu^{2+}$, LSN $(La_3Si_6N_{11}:Ce^{3+})$, LYSN $((La,Y)_3Si_6N_{11}:Ce^{3+})$, CASN $(CaAlSiN_3:Eu^{2+})$, SCASN $((Sr,Ca)AlSiN_3:Eu^{2+})$, KSF $(K_2SiF_6:Mn^{4+})$, CSO $(CaSc_2O_4:Ce^{3+})$, β-SiAlON $((Si,Al)_3(O,N)_4:Eu^{2+})$, Yttrium Aluminum Garnet $(YAG:Y_3(Al,Ga)_5O_{12}:Ce^{3+})$, Lutetium Aluminum Garnet $(LuAG:Lu_3Al_5O_{12}:Ce^{3+})$ and SBCA $((Sr,Ba)_{10}(PO_4)_6C_{12}:Eu^{2+})$. Some optical brightening agents are chemical derivatives of stilbene, coumarin, 1, 3 diphenyl pyrazoline, naphthalene dicarboxylic acid, heterocyclic dicarboxylic acid, and cinnamic acid. Additional light converting materials for use with OLEDs include, for example, phosphorescent materials, fluorophores, fluorescent dyes, conductive polymers, and organometallic phosphors.

FIGS. 16 and 21 serve as examples of color coordinates and ranges of color coordinates that could be achieved in practice in some embodiments of the disclosure. It should be understood that these are examples of some existing standards of color coordinates that can be achieved; other standards that exist or may be developed in the future for white light may be used. Additionally, the disclosed device may be approximately matched in color coordinates to CIE standard illuminants and/or standard illuminant families; it should be noted that the disclosed device may not match all defined characteristics of a standard illuminant, but in some embodiments will approximately match the x,y color coordinates. Some of these additional CIE standard illuminants include but are not limited to A, B, C, D50, D55, D65, D75, E, F1, F2, F3, F4, F5, F6, F7, F8, F9, F10, F11, and F12.

In another aspect of the disclosure, a light emitting device of the disclosure which contains at least two light emitters, each with their own light-converting material, can be configured such that the light emitted from a first light emitter (e.g., a first semiconductor die) and through a first light-converting material (e.g., a first phosphor) ultimately emits at one color temperature (e.g., 2200K) and the light emitted from a second light emitter (e.g., a second semiconductor die) and through a second light-converting material (e.g., a second phosphor) ultimately emits at another color temperature (e.g., 6500K). In such an example device, the amount of power provided to each light emitter (e.g., each semiconductor die within one single LED package) can vary independently of each other. This allows the white light emitting device, in one embodiment, to be color temperature tunable. In the case of the example, tunable between 2200K (warm) and 6500K (cool).

The foregoing description of various aspects of the disclosure has been presented for the purpose of illustration and description. It is not intended to be exhaustive or to limit the disclosure to the precise form disclosed, and obviously, many modifications and variations are possible. Such variations and modifications that may be apparent to one skilled in the art are intended to be included within the scope of the present disclosure as defined by the accompanying claims.

We claim:

1. A light emitting device that inactivates microorganisms, the light emitting device comprising:
    an array of light emitters configured to emit a first light comprising a first peak wavelength in a range of 380 nanometers (nm) to 420 nm; and
    a light converting layer disposed over the array of light emitters, the light converting layer comprising:
        a first light-converting material configured to convert only a first portion of the first light to at least a second light comprising a second peak wavelength different from the first peak wavelength; and
        a second light-converting material configured to convert only a second portion of the first light to at least a third light comprising a third peak wavelength different from the first peak wavelength;
        wherein the first light converting material and the second light converting material are homogenously mixed together to form the light converting layer, and
        wherein at least the first light, the second light, and the third light mix to form a disinfecting white light.

2. The light emitting device of claim 1, wherein the light emitting device is a chip-on-board LED.

3. The light emitting device of claim 1, wherein the array of light emitters comprises at least four light emitters.

4. The light emitting device of claim 1, wherein a light emitter is comprised of a semiconductor die.

5. The light emitting device of claim 1, further comprising a third light converting material within the light converting layer configured to convert only a third portion of the first light to at least a fourth light comprising a peak wavelength different from the first, the second, and the third peak wavelength, wherein the first light, the second light, the third light, and the forth light mix to form a disinfecting white light.

6. The light emitting device of claim 1, wherein the first light makes up at least 20% of the disinfecting white light.

7. The light emitting device of claim 1, wherein the disinfecting white light comprises a CRI value of at least 90.

8. The light emitting device of claim 1, wherein the disinfecting white light comprises a radiometric energy sufficient to inactivate microorganisms.

9. The light emitting device of claim 1, wherein at least 50% of the first light is comprised of wavelengths in the range of 380 nm to 420 nm.

10. The light emitting device of claim 1, further comprising a substrate, wherein the array of light emitters is disposed onto the substrate.

11. A light emitting device that inactivates microorganisms, the light emitting device comprising:
    a substrate; and
    an array of light emitters disposed on the substrate and configured to emit a same first light comprising a first peak wavelength in a range of 380 nanometers (nm) to 420 nm; and
    a light converting layer disposed over at least a portion of the array of light emitters, the light converting layer comprising:
    a first light converting material configured to convert only a first portion of the first light to at least a second light comprising a second peak wavelength different from the first peak wavelength; and a second light converting material configured to convert only a second portion of the first light to at least a third light comprising a peak wavelength different from the first and second peak wavelength; and wherein the first light converting material and the second light converting material are homogenously mixed together to form the light converting layer, wherein at least the first light, the second light, and the third light mix to form a disinfecting white light.

12. The light emitting device of claim 11, wherein a portion of the array of light emitters is not covered by the light converting layer.

13. The light emitting device of claim 11, wherein the light emitting device is a chip-on-board LED.

14. The light emitting device of claim 11, wherein the array of light emitters comprises at least four light emitters.

15. The light emitting device of claim 11, wherein a light emitter is comprised of a semiconductor die.

16. The light emitting device of claim 11, further comprising a third light converting material within the light converting layer configured to convert only a third portion of the first light to at least a fourth light comprising a peak wavelength different from the first, the second, and the third peak wavelength, wherein the first light, the second light, the third light, and the forth light mix to form a disinfecting white light.

17. The light emitting device of claim 11, wherein the first light makes up at least 20% of the disinfecting white light.

18. The light emitting device of claim 11, wherein the disinfecting white light comprises a CRI value of at least 90.

19. The light emitting device of claim 11, wherein the disinfecting white light comprises a radiometric energy sufficient to inactivate microorganisms.

20. The light emitting device of claim 11, wherein at least 50% of the first light is comprised of wavelengths in the range of 380 nm to 420 nm.

* * * * *